US012066394B2

(12) United States Patent
Osswald et al.

(10) Patent No.: US 12,066,394 B2
(45) Date of Patent: Aug. 20, 2024

(54) GAS DETECTION DEVICE WITH A DETECTOR AND A COMPENSATOR AND GAS DETECTION PROCESS

(71) Applicant: Dräger Safety AG & Co. KGaA, Lübeck (DE)

(72) Inventors: Jürgen Osswald, Lübeck (DE); Malte Baesler, Lübeck (DE)

(73) Assignee: DRÄGER SAFETY AG & CO. KGAA, Lübeck (DE)

( * ) Notice: Subject to any disclaimer, the term of this patent is extended or adjusted under 35 U.S.C. 154(b) by 185 days.

(21) Appl. No.: 17/707,406

(22) Filed: Mar. 29, 2022

(65) Prior Publication Data
US 2022/0326169 A1 Oct. 13, 2022

(30) Foreign Application Priority Data
Mar. 30, 2021 (DE) .......................... 102021108008.8

(51) Int. Cl.
*G01N 27/16* (2006.01)
*G01N 33/00* (2006.01)

(52) U.S. Cl.
CPC ......... *G01N 27/16* (2013.01); *G01N 33/0031* (2013.01); *G01N 33/0075* (2013.01)

(58) Field of Classification Search
CPC . G01N 27/16; G01N 33/0031; G01N 33/0075
See application file for complete search history.

(56) References Cited

U.S. PATENT DOCUMENTS

| 7,041,256 B2 | 5/2006 | Wang et al. |
| 10,578,573 B2 | 3/2020 | Zanella, Sr. |
| 2005/0155405 A1* | 7/2005 | Sasaki ............... H01M 8/04089 73/1.06 |

(Continued)

FOREIGN PATENT DOCUMENTS

| DE | 102013008425 B3 | 5/2014 |
| DE | 102013018457 A1 | 5/2015 |

(Continued)

OTHER PUBLICATIONS

JP-2017142274-A-english (Year: 2017).*

*Primary Examiner* — Kristina M Deherrera
*Assistant Examiner* — Fatemeh Esfandiari Nia
(74) *Attorney, Agent, or Firm* — McGlew and Tuttle, P.C.

(57) ABSTRACT

A gas detection device and a process monitor an area for a combustible target gas. A heating segment of a detector (10) is heated when electrical current flows therethrough. A heating segment of a compensator (1) is heated when electrical current flows therethrough. An electrical voltage is applied to both the detector and the compensator. The heating of the detector (10) causes a combustible target gas to be oxidized in an interior of the gas detection device. A detection variable, which depends on the temperature (Temp_10) of the detector, and a detection variable, which depends on the temperature (Temp_11) of the compensator, are measured. A presence and/or a concentration of a target gas are determined as a function of the detection variables. A quality parameter is measured and increases as the detection variable depending on the detector temperature increases and as the detection variable depending on the compensator temperature decreases.

19 Claims, 13 Drawing Sheets

(56) References Cited

U.S. PATENT DOCUMENTS

| | | | | |
|---|---|---|---|---|
| 2009/0035184 A1* | 2/2009 | Koda | ............... | G01N 27/16 |
| | | | | 422/94 |
| 2009/0188297 A1* | 7/2009 | Willett | ............... | G01N 27/16 |
| | | | | 73/23.31 |
| 2018/0128763 A1 | 5/2018 | Swanson et al. | | |
| 2020/0088669 A1* | 3/2020 | König | ............... | G01N 33/0062 |
| 2020/0393432 A1 | 12/2020 | Swanson et al. | | |
| 2023/0349853 A1* | 11/2023 | Santoro, Jr. | ............ | G01N 27/18 |

FOREIGN PATENT DOCUMENTS

| | | | |
|---|---|---|---|
| DE | 102017005713 A1 | | 12/2018 |
| DE | 102018122860 A1 | | 3/2020 |
| JP | 2012177634 A | | 9/2012 |
| JP | 2017142274 A | * | 8/2017 |

* cited by examiner

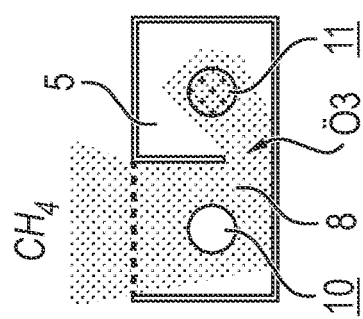 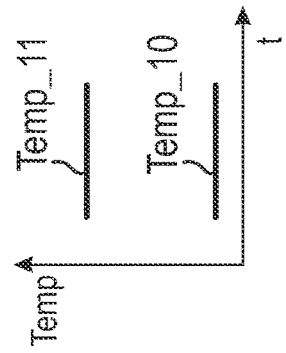
FIG. 10a
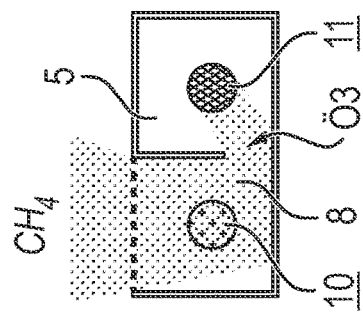 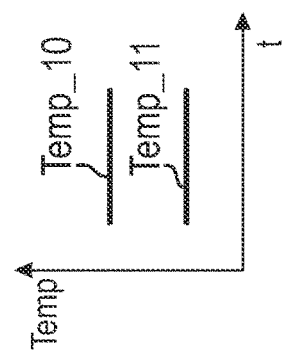
FIG. 10b
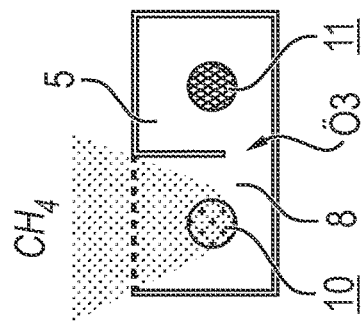 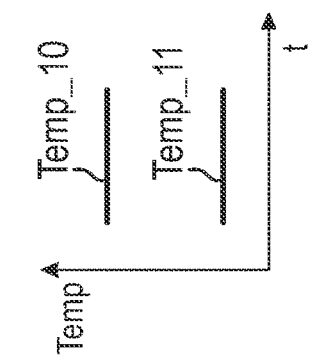
FIG. 10c
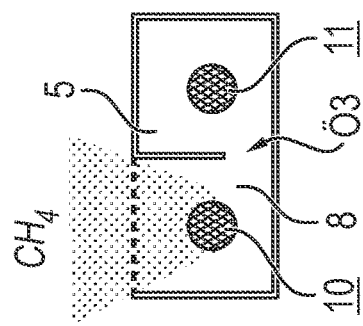 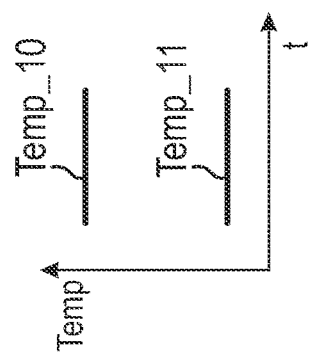
FIG. 10d
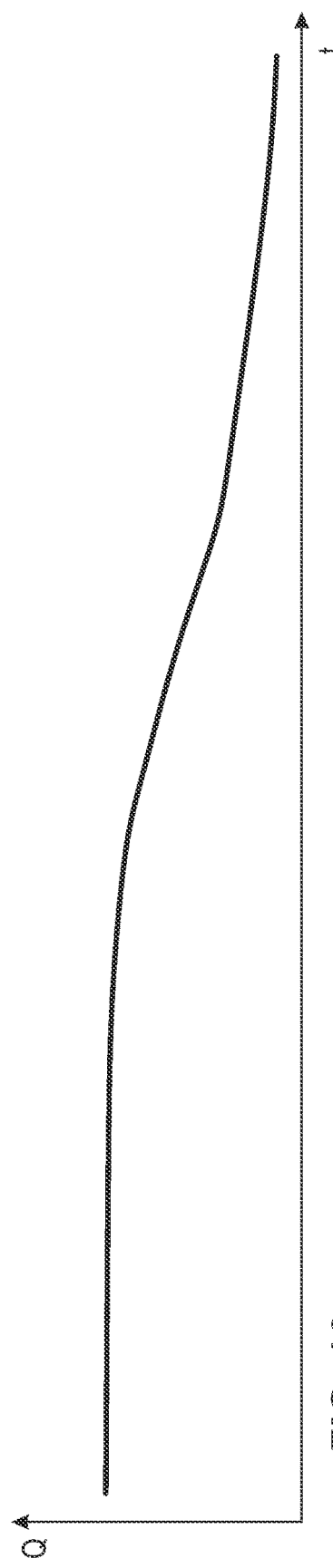
FIG. 10e

GAS DETECTION DEVICE WITH A DETECTOR AND A COMPENSATOR AND GAS DETECTION PROCESS

CROSS REFERENCE TO RELATED APPLICATIONS

This application claims the benefit of priority under 35 U.S.C. § 119 of German Application 10 2021 108 008.8, filed Mar. 30, 2021, the entire contents of which are incorporated herein by reference.

TECHNICAL FIELD

The present invention pertains to a gas detection device and to a gas detection process, which are capable of monitoring an area for at least one defined gas, hereinafter called a target gas to be detected, wherein the target gas or a target gas is combustible in a temperature range that may occur in the area to be monitored and is oxidized by the gas detection device and is detected thereby. The area to be monitored is, for example, a mine, a refinery or a heating system operated with combustible gas, a warehouse or even a transportation vehicle. The present invention further pertains to a process, which is carried out with the use of such a gas detection device.

TECHNICAL BACKGROUND

Gas detection devices which comprise a detector and a compensator have become known. Both the detector and the compensator are heated. The detector is capable of oxidizing a combustible target gas to be detected, and the thermal energy, which is released during the oxidation, increases the temperature of the detector. This increase in temperature is measured and is an indicator of a combustible target gas. A gas detection device with such a detector is also called a "heat tone sensor."

The compensator is configured such that it does not oxidize the target gas during heating at all or it does so only to a lesser extent than does the detector. The gas detection device is exposed, as a rule, to a varying ambient temperature and is in many cases exposed to additional varying ambient conditions, e.g., to ambient humidity. The varying ambient conditions affect both the detector and the compensator. Measured values of the compensator are used to compensate the effect of varying ambient conditions on the measured values of the detector by calculation. The gas detection device according to the present invention and the gas detection process according to the present invention also utilize this principle.

One problem of a gas detection device with a detector and with a compensator is that the detector is in many cases subject to aging in the course of use and its electrical and/or chemical properties will therefore change. A frequent cause for the aging is that the heated detector reacts chemically with a harmful gas, for example, with a siloxane or with a hydrogen sulfide and it changes as a result. This change is sometimes also called "poisoning" of the gas detection device. For example, deposits are formed on the surface of the detector due to the heating and even a layer of glass is formed in case of intense poisoning. This poisoning does, as a rule, take place gradually (as a drift) rather than abruptly.

A sensor 10 with a first pellistor element 1, with a second pellistor element 2 and with a heating element 3 is described in DE 10 2018 122 860 A1. The first pellistor element 1 comprises a catalyst element 5 in the form of a pellet on a diaphragm 7. The second pellistor element 2 is used in one embodiment as a reference pellistor element and it is free from a catalyst element. The two pellistor elements 1, 2 respond to ambient temperature and/or to changes in humidity in the same manner. A temperature sensor element 4 is capable of measuring the temperatures of the two pellistor elements 1, 2. The first pellistor element 1 burns a target gas. The additional heat, which is generated thereby on the surface of the catalyst element, is detected by means of the temperature sensor element and is used to generate a sensor signal, which is proportional to the gas concentration.

A siloxane layer can become deposited on the heated surface of the catalytic first pellistor element 1, as a result of which the first pellistor element 1 is poisoned. Different electrical voltages are applied one after another during a checking to the first pellistor element 1 in order to detect this, as a result of which a continuous or stepped temperature course (stepped temperature curve) is obtained. The response of the first pellistor element 1 is compared to a response of an unpoisoned pellistor element.

SUMMARY

A basic object of the present invention is to provide a gas detection device for detecting a combustible target gas, wherein the gas detection device comprises a detector and a compensator and wherein the detector is configured to oxidize a combustible target gas. It shall be made possible here for the detection results of the gas detection device according to the present invention to be influenced by a gradual change of the detector in the course of use to a lesser extent than are those of prior-art gas detection devices. Furthermore, the basic object of the present invention is to provide a gas detection process with a corresponding gas detection device.

The object is accomplished by a gas detection device having the features according to the invention and by a gas detection process having the features according to the invention. Advantageous embodiments of the gas detection device according to the present invention are, insofar as meaningful, also advantageous embodiments of the gas detection process according to the present invention and vice versa.

The gas detection device according to the present invention is configured to monitor a spatial area for at least one combustible target gas to be detected. The process according to the present invention is carried out with the use of a gas detection device according to the present invention. This area is monitored by the process for the target gas.

The gas detection device comprises a detector and a compensator. The gas detection device is configured such that a gas mixture can flow from the area to be monitored into the interior of the gas detection device and it can there reach both the detector and the compensator. Both the detector and the compensator are in a fluidic connection each with the area to be monitored. As a result, a gas mixture from the area to be monitored can reach both the detector and the compensator.

Both the detector and the compensator each comprise a heating segment. This heating segment is heated when electrical current flows through the heating segment.

The gas detection device is configured to apply a respective electrical voltage both to the detector and to the compensator, doing so independently from one another in one embodiment, so that the electrical voltages applied may be different. The electrical voltage applied to the detector causes an electrical current to flow through the heating segment of the detector (detector heating segment) and it heats the detector heating segment. The electrical voltage applied to the compensator causes an electrical current to flow through the heating segment of the compensator (compensator heating segment) and it heats the compensator heating segment.

The detector is configured as follows: When the detector heating segment is being heated, a combustible target gas, which is located in the interior of the gas detection device, is oxidized thereby. Thermal energy is released during this oxidation, and this thermal energy acts on the detector heating segment and raises the temperature of the detector heating segment compared to a state in which no target gas is present and the detector heating segment is heated only by the flowing current.

In a first alternative of the present invention, the compensator is capable of oxidizing a combustible target gas but to a lesser extent than is the detector or it is not capable of oxidizing a combustible target gas same at all. Therefore, less thermal energy or even no thermal energy generated by an oxidation acts on the compensator heating segment even if a combustible target gas is present in the interior of the gas detection device.

In a second alternative, the gas detection device is configured such that a smaller quantity of a combustible target gas reaches the compensator than reaches the detector from the area to be monitored. For example, a fluidic connection between the compensator and the area to be monitored has a smaller cross-sectional area than does a fluidic connection between the detector and the area to be monitored, so that a smaller volume flow is obtained. Or else, the compensator is separated from the area to be monitored such that a gas mixture from the area to be monitored can reach the compensator only by passing the detector but not directly from the area to be monitored. The detector and the compensator may be configured in this embodiment of the second alternative such that they are capable of oxidizing a combustible target gas at an equal extent. They may have different configurations in the second alternative as well. Since a gas mixture from the area can reach the compensator only by flowing past the detector, the detector heating segment already oxidizes at least a portion of a combustible target gas before this target gas can reach the compensator.

The first alternative and the second alternative may be combined with one another. Different embodiments of the second alternative may likewise be combined with one another.

The gas detection device further comprises a sensor arrangement (sensor array). This sensor arrangement is capable of measuring two detection variables. The one measured detection variable depends on the temperature of the detector heating segment. The other measured detection variable depends on the temperature of the compensator heating segment. The detection variable or a detection variable may also be the temperature itself. Examples of a detection variable that depends on the temperature are the electrical voltage applied, the current intensity of the flowing electrical current, the electrical power absorbed, and the electrical resistance. The electrical resistance is known to depend on the temperature in many current-conducting materials.

The same detection variable or different detection variables may be used for the detector and for the compensator. Even if the same detection variable is used, this variable assumes, as a rule, different values for the detector and for the compensator when a combustible target gas is present and is oxidized by the detector.

The gas detection device comprises a signal-processing analysis unit (evaluation unit). This analysis unit may be a part of the gas detection device or be located at a location remote in space from the gas detection device. The analysis unit is configured to automatically carry out at least one of the following two steps:

The analysis unit determines (decides) whether or not at least one predefined combustible target gas is present in the area to be monitored—more precisely, whether the concentration or a variable correlated with the concentration is above a construction-dependent detection threshold or predefined threshold or not.

The analysis unit determines at least approximately the concentration of the combustible target gas or of at least one combustible target gas in the area to be monitored.

The analysis unit uses values of the two measured detection variables for this decision and/or determination.

Furthermore, the analysis unit is capable of automatically calculating at least once a quality parameter for the quality of the gas detection device. The calculation or a calculation and preferably each repeated calculation of the quality parameter is carried out by the analysis unit as a response to the fact that it has detected a combustible target gas, for example, as a response to the fact that a determined concentration of a target gas is above a predefined concentration threshold.

The analysis unit carries out the calculation of the quality parameter depending on the two detection variables. For example, it uses measured values or time courses (time curves) of the two detection variables. The analysis unit calculates the quality parameter such that the quality parameter increases with increasing detection variable, which depends on the temperature of the detector heating segment, and with decreasing detection variable, which depends on the temperature of the compensator heating segment.

If the compensator heating segment is not configured to oxidize a combustible target gas to an appreciable extent, the quality parameter preferably increases with decreasing value of the detection variable that depends on the temperature of the compensator heating segment.

The gas detection device calculates according to the present invention the quality parameter such that the quality parameter increases as the detection variable that depends on the detector temperature increases, and as the detection variable that depends on the compensator temperature, or as the value of this detection variable, decreases. Calculation of a deterioration parameter by the gas detection device has the same effect. This deterioration parameter increases with decreasing detection variable that depends on the detector temperature, and with an increase in the detection variable that depends on the compensator temperature.

The analysis unit then calculates the quality parameter in the manner just described when the two detection variables have been set such that they increase with an increase in the respective temperature of the heating segment. This is the case with many meaningful detection variables. If conversely, the two detection variables decrease with an increase in the respective temperature, then the analysis unit calculates the quality parameter as follows: The quality parameter increases as the detector detection variable depending on the detector temperature decreases and as the compensator detection variable depending on the compensator temperature or as the value of this detection variable increases.

According to the present invention, the sensor arrangement measures two detection variables, namely, a detector detection variable that depends on the temperature of the detector, and a compensator detection variable that depends on the temperature of the compensator. The gas detection device is configured such that the detector temperature increases more greatly in the presence of at least one combustible target gas than does the compensator temperature, providing that the detector is not poisoned completely or almost completely. This greater temperature rise is brought about by the oxidation of the target gas by the detector. Varying ambient conditions, especially a varying ambient temperature and a varying ambient humidity, do, by contrast, act on the detector and on the compensator in approximately the same manner. Consequently, the measurement of the detection variable for the compensator makes it possible to compensate the effect of the ambient conditions on the detection variable, which depends on the detector temperature, by calculation at least approximately.

According to the present invention, the gas detection device calculates the quality parameter at least once as a response to the fact that it has detected a combustible target gas. The calculation according to the present invention of the quality parameter does not require the concentration or the type of the detected target gas to be known. In particular, the calculation of the quality parameter does not require the area to be monitored to be free from a combustible target gas while the two detection variables are being measured. The quality parameter is rather calculated as a response to the detection of a combustible target gas.

The gas detection device according to the present invention is therefore capable of calculating the quality parameter even during the ongoing use and not only during a checking or calibration or adjustment, during which a gas mixture, which contains a combustible target gas with a known concentration and of a known type is being fed to the gas detection device. It is possible thanks to the present invention for the gas detection device to monitor itself continuously during use and to calculate the quality parameter repeatedly continually, namely, each time whenever it has detected a target gas.

A manner in which a detector can be poisoned, i.e., a manner in which siloxanes are deposited on a surface of the detector, in the course of its use is described in DE 10 2018 122 860 A1. Another or additional manner of poisoning may occur when the detector is capable of oxidizing combustible target gases by means of a catalytically active material. Hydrogen sulfide can compromise the catalytic effect of the detector. In addition, the detector may be subject to sintering.

The quality parameter calculated according to the present invention depends on the detection variable, which is also used for the detection of the target gas. Poisoning of the detector, therefore, affects this detection variable. A consequence is that different possible types of poisonings can frequently be detected rather than only a poisoning based on a deposition of siloxanes and/or of combustion products of siloxanes on the surface.

The functional detector according to the present invention oxidizes a combustible target gas, which is located in the interior of the gas detection device. Thermal energy is released during this oxidation. This thermal energy being released raises the temperature of the detector heating segment and affects the detection variable, which depends on the detector temperature.

Material is deposited in many cases on the heated surface of the detector over the course of use, for example, this may be due to the heated surface contacting siloxanes or hydrogen sulfides or other harmful gases. Since material is deposited on the detector surface, the detector is capable in many cases of oxidizing less combustible target gas over the course of use. The detector is gradually "poisoned." As a result, less thermal energy is also released, the detector heating segment is heated less intensely from the outside, and the temperature of the poisoned detector rises at equal concentration of the target gas less markedly than in case of a new detector. The increasing poisoning of the detector, therefore, leads to a lower sensitivity of the gas detection device for combustible target gases.

If the detection variable increases with rising temperature, the combustible target gas leads to a smaller increase in this detection variable than in case of a detector that is not poisoned. The quality parameter is an indicator of this reduced sensitivity of the gas detection device for a combustible target gas, and it decreases based on the poisoning. The deterioration parameter becomes correspondingly higher.

On the other hand, the temperature of the detector heating segment and hence also the detection variable, which depends on the detector temperature, depend on the ambient conditions. In order to compensate this effect by calculation, the quality parameter additionally depends on the detection variable that is correlated with the temperature of the compensator heating segment. The effect of the compensator temperature on the quality parameter is inversely proportional to the effect of the detection temperature. The effect of ambient conditions on the quality parameter is therefore largely compensated by calculation.

In a first alternative of the present invention, the compensator is capable of oxidizing a combustible target gas to a lesser extent than is the detector. In a variant of the first alternative, the compensator is even fully incapable of oxidizing a combustible target gas. In a second alternative of the present invention, a smaller quantity of a combustible target gas reaches the compensator from the area to be monitored compared to the quantity reaching the detector.

The compensator is poisoned more slowly than is the detector in both alternatives. If the compensator is not capable of oxidizing any combustion target gas, it is not poisoned by a combustible target gas at all or it is not poisoned at least to a substantial extent. An embodiment of the gas detection device in which the unpoisoned compensator is capable of oxidizing a combustible target gas to the same extent as the unpoisoned detector is also possible. In one form of this embodiment, a gas mixture from the area to be monitored reaches the compensator only by flowing by the detector rather than directly, and the detector oxidizes at least a part of a combustible target gas before the combustible target gas reaches the compensator. This effect occurs as long as the detector is not yet completely poisoned. In another form of this embodiment, the volume flow from the area to be monitored to the compensator is smaller than the volume flow from the area to the detector, so that less combustible target gas will, for this reason, reach the compensator than the detector, and it also happens when the detector is already poisoned to a considerable extent. The diffusion or the transportation of a gas mixture and hence also of a combustible target gas from the area to be monitored to the compensator is limited more strongly in this embodiment than the diffusion or the transportation to the detector.

The compensator is therefore also poisoned more slowly than the detector in all embodiments in which not only the detector but also the compensator is capable of oxidizing a combustible target gas. The detection variable, which depends on the compensator temperature, changes therefore more slowly in both alternatives of the present invention than does the detection variable, which depends on the detector temperature, while the gas detection device is being used and is exposed to at least one combustible target gas, i.e., over the course of use.

Since both the detector and the compensator are in a respective fluidic connection each with the area to be monitored, both the detection variable depending on the compensator temperature and the detection variable depending on the detector temperature are influenced by possibly varying ambient conditions, especially by the ambient temperature. The feature that the detector detection variable and the compensator detection variable act in opposite manners on the quality parameter compensates in many cases to some extent the effect of the ambient conditions on the quality parameter.

In addition, the effect of the oxidation of the combustible target gas on the detection variable, which depends on the detector temperature, is, as a rule, considerably greater than the effect of ambient conditions, at least as long as the detector is not poisoned to a considerable extent or even completely. Therefore, varying ambient conditions cannot, as a rule, lead to a significantly varying quality parameter. The quality parameter is significantly reduced only by a poisoning.

Many combustible target gases have a higher thermal conductivity than the ambient air and therefore they cool the compensator and to a certain extent the detector as well. The effect of the higher thermal conductivity on the detection variable is opposite to the effect of the oxidation of a combustible target gas on the detection variable in case of such a target gas. As long as the detector is not yet poisoned to a great extent and it, therefore, oxidizes a considerable quantity of a combustible target gas, the higher thermal conductivity has, however, hardly any effect on the detector. The higher thermal conductivity does not, therefore, influence the quality parameter to a considerable extent, either. When the detector is considerably poisoned, the higher thermal conductivity also has a relevant effect on the detector. The configuration according to the present invention of the quality parameter, namely, the opposite effects of the two detection variables, does, by contrast, compensate this effect of this higher thermal conductivity on both the detector and the compensator in this case.

In one embodiment, the quality parameter is related to a defined combustible target gas to be detected. This combustible target gas is predefined, for example, as a reference target gas. As a result, the thermal conductivity of the target gas is known as well. This thermal conductivity additionally depends, as a rule, on the concentration of the target gas in a gas mixture. The quality parameter is also related in this case to a defined concentration, for example, to a predefined lower detection threshold. This embodiment increases the reliability of the quality parameter calculated according to the present invention especially when the compensator is not capable of oxidizing any target gas.

In one embodiment, the analysis unit automatically uses the quality parameter to compensate the effect of a poisoning on a detection result at least approximately by calculation. In particular, the calculated quality parameter is used to compensate a decreasing sensitivity of the gas detection device on a combustible target gas to be detected at least approximately. Since the quality parameter is calculated and used to automatically compensate the decreasing sensitivity, the reliability of the gas detection device is increased. Furthermore, it is possible in many cases to approximately predict a remaining duration of use of the gas detection device on the basis of the quality parameter.

In one embodiment, a quality parameter threshold is predefined and is stored in a memory of the gas detection device. An initial quality parameter is preferably calculated at the time of an initial adjustment of the gas detection device, and the quality parameter threshold is a predefined percentage of the initial quality parameter, which quality parameter threshold is below 100%. It is also possible to predefine a difference from the initial quality parameter or to predefine an absolute quality parameter threshold. When the calculated quality parameter is lower than or equal to this quality parameter threshold, the gas detection device generates a corresponding disturbance message. This disturbance message is outputted in a form perceptible for a human being, for example, by an output unit of the gas detection device itself, or the gas detection device transmits a message with the disturbance message to a receiver located at a spaced location in space, and the receiver outputs the disturbance message in a form perceptible for a human being.

This embodiment reduces the risk of the gas detection device being used for monitoring the area even though the detector is poisoned to such a great extent that the gas detection device is no longer capable of detecting a combustible target gas with sufficient reliability. Furthermore, this embodiment eliminates in many cases the need to have to replace the gas detection device after a predefined duration of use, regardless of how greatly the detector is poisoned. The gas detection device can rather be used in many cases until it outputs a disturbance message. As a result, the gas detection device can be used longer, and a replacement is necessary less frequently. This is especially advantageous when the gas detection device is used at a difficult-to-access location. On the other hand, it is ensured with a higher reliability that a poisoned gas detection device is no longer used.

The gas detection device preferably transmits at regular intervals a message to the receiver in order to signal that it is still able to function and is, in particular, still supplied sufficiently with electrical energy and is capable of transmitting messages. In one embodiment, this message additionally comprises the respective last calculated quality parameter. This embodiment makes it possible for a human being to monitor the gas detection device from a distance.

In one embodiment, the gas detection device outputs a determined value for the concentration of a combustible target gas in a form perceptible for a human being, wherein this concentration value was determined as a function of the calculated quality parameter. In one embodiment, the determined concentration value is converted into % LEL (LEL=lower explosion limit) and a value in % LEL is outputted.

It is also possible that the gas detection device outputs a measured or calculated value for the concentration of a combustible target gas in a manner perceptible for a human being and additionally an evaluation of this outputted concentration value, wherein this evaluation depends on the calculated quality parameter. For example, a symbol or the concentration value is outputted in a special manner when the quality parameter is below a predefined threshold. This alternative makes it possible, but it makes it unnecessary to compensate a measured value by means of the calculated quality parameter.

In addition, it is possible to operate the gas detection device in one of two different modes as desired, namely, in a normal mode or in an exceptional mode. If the quality parameter is above a predefined quality threshold, the gas detection device is operated in the normal mode, and the analysis unit uses for the detection values of two detection variables. The gas detection device is operated otherwise in the exceptional mode. In one embodiment, the analysis unit uses values of both detection variables in the exceptional mode as well, but it applies a different decision rule, for example for a weighted combination unlike for a difference of the two detection variables as in the normal mode. In another embodiment, the analysis unit only uses in the exceptional mode values of the detection variable, which depends on the compensator temperature. Consequently, the detection variable dependent on the detector temperature is not used anymore in case of a low quality parameter.

In a preferred embodiment, the analysis unit calculates a detector compensated detection variable, which depends on the detector temperature, as well as a compensator compensated detection variable, which depends on the compensator temperature. Two reference values are used for this, namely, a detector reference value and a compensator reference value. The detector reference value is a value which the detection variable depending on the detector temperature assumes when no combustible target gas is present. The compensator reference value is a value which the detection variable dependent on the compensator temperature assumes when no combustible target gas is present. The two reference values preferably pertain to the same ambient conditions.

The embodiment with the two compensated detection variables makes it possible to compensate such differences between the detector and the compensator by calculation which are due to the device construction or the device manufacture. These differences affect the two reference values. The embodiment, therefore, eliminates the need for the detector and for the compensator to have an identical configuration electrically. In particular, it is not necessary for the detector and for the compensator to have the same electrical resistance. The reference values compensate especially configuration-related differences between the detector and the compensator.

The analysis unit is configured according to the present invention to detect the presence of a combustible target gas and/or it is configured to determine the concentration of the target gas. The analysis unit uses the two measured detection variables for the detection or determination.

In one embodiment, the analysis unit detects the target gas or additionally determines the target gas concentration as a function of a parameter. This parameter depends on the calculated quality parameter and influences the sensitivity of the gas detection device for a combustible target gas. For example, the analysis unit determines the target gas concentration such that the target gas concentration is equal to the product of the parameter and the difference between the two detection variables or to the two compensated detection variables. The parameter is consequently a factor. This parameter (more precisely, the value of this parameter) depends on the calculated quality parameter, doing so preferably such that the parameter increases with decreasing quality parameter.

The parameter is preferably the product of a correlation factor and a correction factor. The correlation factor is valid for a defined, unpoisoned copy (example/instance) of the gas detection device and provides the concentration depending on the two detection variables, for example, on the difference between the two detection variables in case of an unpoisoned detector. The correlation factor may vary from copy to copy. The correction factor depends on the quality parameter, doing so preferably such that the correction factor increases with decreasing quality parameter. The correction factor may be valid for an entire product line or for a production lot of gas detection devices according to the present invention. The correction factor preferably has the value 1 in case of a new and therefore unpoisoned detector.

This dependence of the parameter on the quality parameter compensates by calculation up to a certain extent the effect of a possible increasing poisoning of the detector of the gas detection device on the determination of the concentration. When the parameter increases with decreasing quality parameter, a decreasing sensitivity of the gas detection device for a target gas is compensated to a certain degree.

In one embodiment, the gas detection device detects a combustible target gas when the difference between the value of the detection variable depending on the detector temperature and the value of the detection variable depending on the compensator temperature is outside of a tolerance range. The difference of the values of the compensated detection variables is preferably formed. This tolerance range depends on the quality parameter. The tolerance range preferably becomes narrower as the quality parameter decreases. An initial tolerance range, which is valid for an unpoisoned gas detection device, i.e., in case of a maximum quality parameter, is especially preferably predefined. A currently used tolerance range is calculated depending on the initial tolerance range and on the calculated quality parameter. A decreasing sensitivity of the gas detection device based on the increasing poisoning is partially compensated by calculation in this embodiment as well, namely, by the tolerance range being made narrower. An alarm is preferably outputted in a form perceptible for a human being when the difference is outside of the tolerance range.

Depending on the quality parameter, two tolerance ranges, namely, a narrower tolerance range and a broader tolerance range, are calculated in a variant of this embodiment, wherein the narrower tolerance range is located within the broader tolerance range. Both tolerance ranges are calculated as a function of the quality parameter. If the difference is outside of the broader tolerance range, an alarm is preferably outputted. If the difference is outside of the narrower tolerance range but is within the broader tolerance range, a pre-alarm is outputted. Thanks to this embodiment, a user has more time in many cases for taking appropriate countermeasures, for example, in order to end the discharge of combustible target gas or in order to evacuate a room. For example, the gas detection device shows a green, yellow, or red indicator light as desired (green if no target gas was detected, yellow for a pre-alarm and red for an alarm).

The detector is preferably arranged in the interior of a stable housing. This housing is capable of withstanding the heat that is generated when electrical current is flowing through the detector and the heated detector is oxidizing a combustible target gas. This housing is preferably also capable of withstanding an explosion of combustible target gas in the interior of the housing. This housing is in a fluidic connection with the area to be monitored. A gas mixture can enter into the interior of the housing through this fluidic connection. The detector is capable of oxidizing a combustible target gas, which is present in the interior of this housing.

The compensator is preferably also arranged in a housing, namely, either in the same housing as the detector or in a separate housing. In case of a separate compensator housing, this compensator housing is also in a fluidic connection with the area to be monitored. In one embodiment, the fluidic connection between the compensator housing and the area to be monitored passes through the detector housing. As long as the detector is not poisoned or is poisoned only relatively slightly, no combustible target gas will then reach the compensator, because the detector oxidizes this target gas.

Two separate housings preferably insulate the detector and the compensator thermally from one another. If the detector and the compensator are arranged in the same housing, a thermal barrier is preferably arranged between the detector and the compensator. The effect of an oxidation of the target gas on the detection variable of the compensator is reduced in both cases.

An outer housing, e.g., one made of a solid plastic, preferably encloses the solid housing for the detector and for the compensator, and for additional components of the gas detection device.

In one embodiment, the gas detection device comprises, in addition to the detector, an additional detector with a heating segment. The gas detection device is also capable of applying an electrical voltage, which causes electrical current to flow and to heat the heating segment, to the heating segment of the additional detector. In one embodiment, electrical voltages can be applied to the detector, to the additional detector and to the compensator independently from one another. The heated additional detector is also capable of oxidizing a combustible target gas. The compensator makes it possible for the analysis unit to compensate by calculation the effect of varying ambient conditions on both the detector and on the additional detector. It is not necessary to provide two compensators. The compensator is connected quasi parallel to both detectors.

The additional detector is preferably located in a housing in the interior of the gas detection device, while the detector is arranged outside of this housing. An opening is prepared in this housing, so that a gas mixture and hence also a combustible target gas can reach the additional detector. The opening may be configured such that the fluidic connection between the area to be monitored and the additional detector has a smaller cross-sectional area and hence ensures a smaller volume flow than does the fluidic connection between the area and the detector outside of the housing. As an alternative, a gas mixture from the surrounding area reaches the additional detector only through the housing for the detector. The additional detector is poisoned in both embodiments more slowly than the detector, especially because smaller quantities of harmful gases will reach the additional detector.

The embodiment with two detectors leads to a certain redundancy. If the detector is poisoned, the additional detector is still capable of oxidizing a combustible target gas in many cases, because the additional detector is poisoned more slowly. The duration of use of the gas detection device is prolonged in many cases.

The analysis unit preferably calculates the quality parameter as follows: The quality parameter increases with increasing detection variable, which depends on the temperature of the detector, with the detection variable, which depends on the temperature of the additional detector, or with these two detection variables. In addition, the quality parameter decreases according to the present invention with the decrease of the detection variable, which depends on the temperature of the compensator. This is also true when the detection variable increases with rising temperature.

This embodiment of the quality parameter takes into account the fact that the gas detection device still has a high quality when at least one of the two detectors is still poisoned slightly.

In a variant of this embodiment, the analysis unit calculates two individual quality parameters. The first individual quality parameter increases with increasing detection variable for the detector and with decreasing detection variable for the compensator, and it does not depend on the temperature of the additional detector. The second individual quality parameter increases with increasing detection variable for the additional detector and with decreasing detection variable for the compensator, and it does not depend on the temperature of the detector. The analysis unit calculates the quality parameter as a function of these two individual quality parameters. For example, it uses the higher individual quality parameter or a weighted combination of the two individual quality parameters as the quality parameter. It is also possible that the analysis unit calculates the quotient or the difference from the first individual quality parameter and the second individual quality parameter and uses this quotient as the quality parameter. It is possible that the analysis unit uses the detection variable that depends on the temperature of the detector, only when the first individual quality parameter is sufficiently high, and it otherwise uses the detection variable that depends on the temperature of the additional detector.

In one embodiment, the gas detection device can be operated optionally in a normal mode or in an exceptional mode. The gas detection device switches itself automatically or also after a corresponding user input into the exceptional mode when the quality parameter calculated according to the present invention drops below a predefined quality parameter threshold. The analysis unit determines in the normal mode the presence and/or the concentration of a combustible target gas as a function of a difference between the two detection variables, preferably depending on a difference between the two compensated detection variables. In the exceptional mode, the analysis unit determines, by contrast, the presence and/or the concentration as a function of a weighted combination of the two detection variables, preferably on a weighted combination of the two compensated detection variables or else it uses in the exceptional mode only values of the detection variable, which depends on the compensator temperature.

The embodiment with the exceptional mode avoids the need for putting the gas detection device immediately out of operation when the quality parameter drops below the quality parameter threshold. The device can rather still continue to be operated in the exceptional mode. The gas detection device preferably outputs a warning in a form perceptible for a human being indicating that the gas detection device is in an exceptional mode now.

The detection variable depending on the compensator temperature is used in the normal mode to compensate by calculation at least partially the effect of ambient conditions on the detection variable, which depends on the detector temperature. A quality parameter below the quality parameter threshold is an indicator that the detector is capable of oxidizing a combustible target gas to a relatively low extent only. The gas detection device is preferably switched over into the exceptional mode in case of such a low quality parameter.

In a possible embodiment of the gas detection device, the compensator is also capable of oxidizing a combustible target gas, even though to a lesser extent than the detector. The heated surface of the detector changes harmful gases such that deposits will be formed on the surface of the detector, but the compensator is not damaged substantially.

The detector is often poisoned increasingly, while the compensator is still capable of oxidizing a combustible target gas.

What is formed in this possible embodiment in the exceptional mode is a weighted aggregation of the two detection variables, preferably a weighted combination of the two compensated detection variables, wherein the two weighting factors are greater than zero and the weighting factors preferably depend on the construction of the detector and of the compensator, especially on how strongly the detector is capable of oxidizing a combustible target gas and on how strongly the compensator is capable of oxidizing a combustible target gas.

In another possible embodiment of the gas detection device, the compensator is completely incapable of oxidizing a target gas or it is incapable of oxidizing a target gas to a substantial extent. Another effect of a combustible target gas on the compensator prevails in this possible embodiment, and this effect also acts on the detector. Many combustible target gases to be detected, for example, methane, have a higher thermal conductivity than air. These target gases therefore cool the compensator and also the detector more intensely than does air. In case of the electrical voltage and other meaningful detection variables, this causes the detection variable, which depends on the compensator temperature, to drop. The electrical resistance is known to decrease when the temperature rises in many electrically conductive materials.

The analysis unit calculates a weighted aggregation of the two detection variables in this other possible embodiment as well. The weighting factor for the compensator is, however, lower than zero because the concentration increases with decreasing detection variable. The weighting factor for the detector is preferably greater than zero because in many cases, despite an intense poisoning, the detector is still capable of oxidizing so much target gas that the temperature rise based on the oxidation is greater than the drop in temperature based on the better thermal conductivity of the combustible target gas.

The particular combustible target gas or the particular combustible target gases which the gas detection device shall detect are preferably predefined in this alternative embodiment, in which the compensator is not capable of oxidizing the target gas but the compensator is cooled by the combustible target gas based on the higher thermal conductivity. The gas detection device can optionally be switched over and thereby used for the detection of a particular predefined target gas. When the target gas to be detected is known, its thermal conductivity is, as a rule, known as well. If this thermal conductivity depends on the concentration of the combustible target gas, a lower detection threshold is frequently predefined, for example, as vol. % or % LEL. A lower threshold for the change in the thermal conductivity results from these predefined values based on the combustible target gas. Thanks to this predefined value, the gas detection device is still frequently capable of detecting the presence above the detection threshold of a predefined target gas with known thermal conductivity in the exceptional mode.

The two weighting factors depend, on the one hand, on a correlation factor in both embodiments. This correlation factor indicates how the concentration is linked with the detection variable for the detector and for the compensator. The two weighting factors—or at least the weighting factor for the detector preferably depend/depends additionally on a correction factor, the correction factor depending on the quality parameter and being preferably greater at lower quality parameters.

It is possible in many cases in both possible embodiments to still use the gas detection device even in case of a poor quality parameter.

The gas detection device may be configured as a portable device and comprise a separate power supply unit. A human being can carry this gas detection device along when he or she enters into an area that may contain a combustible target gas. The gas detection device preferably outputs an alarm in a form perceptible for a human being when it has detected a combustible target gas.

It is also possible that the gas detection device is configured as a stationary device. This embodiment makes it possible to connect the gas detection device to a stationary power supply unit. The gas detection device does not necessarily need to comprise a separate power supply unit.

The present invention will be described below based on exemplary embodiments. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIGS. 10a, 10b, 10c, 10d and 10e are views showing that the detector temperature decreases and the compensator temperature rises based on an increasing poisoning of the detector;

DESCRIPTION OF PREFERRED EMBODIMENTS

Figure 1:
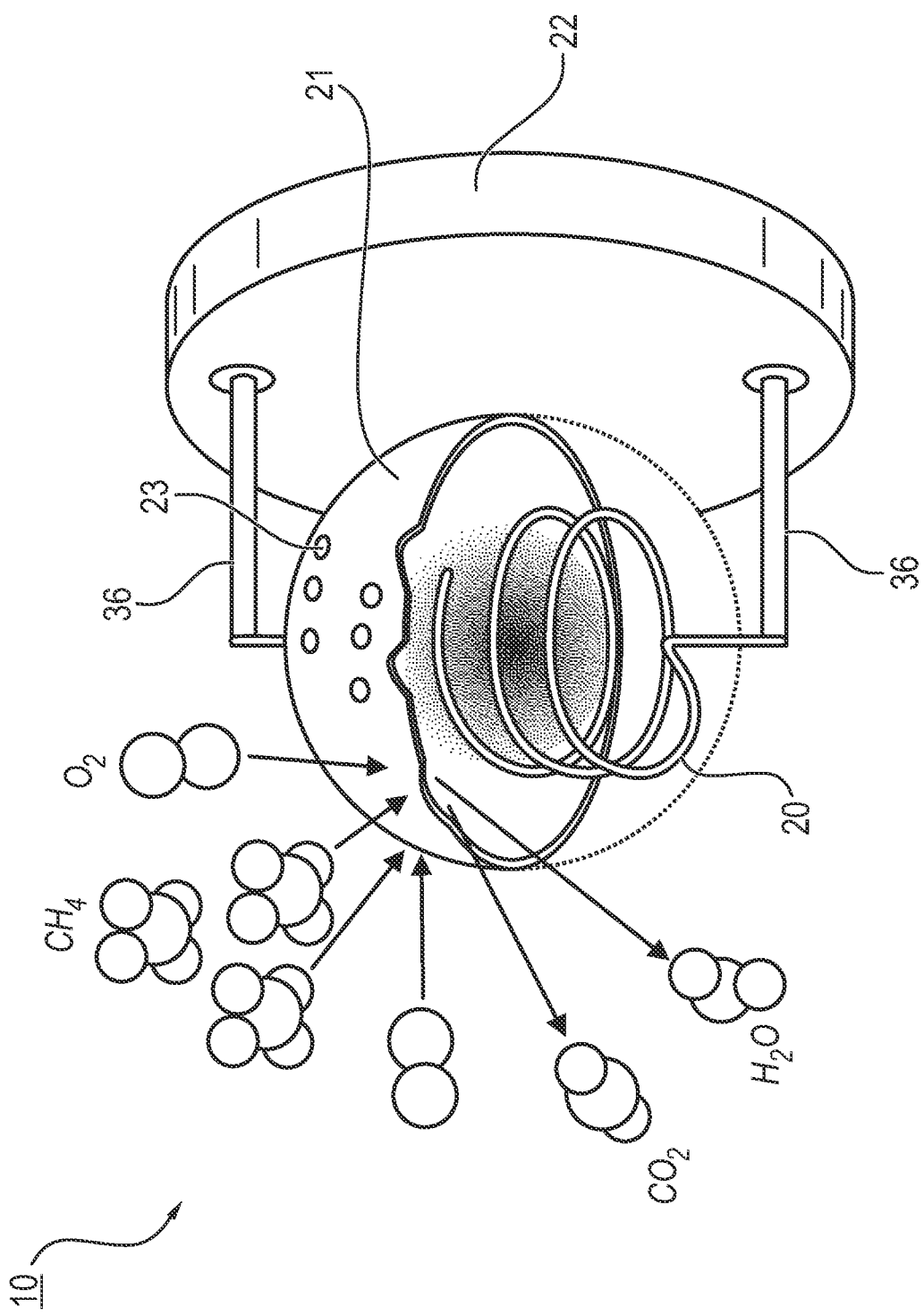
FIG. 1 is a partial cutaway view showing an example of a detector configured as a pellistor.

The gas detection device according to the present invention is capable of monitoring a three-dimensional area for the presence of at least one combustible target gas and/or of determining the concentration of a combustible target gas. The gas detection device uses a process known from the state of the art for analyzing a gas mixture in the area.

A detector is located in the interior of a housing of the gas detection device. A gas mixture flows through an opening from the area to be monitored into the interior of the housing. The detector comprises an electrically conductive wire with a heating segment. The detector heating segment is, for example, a coil, which forms a segment of the wire. The electrically conductive material is, for example, platinum or a mixture which contains platinum. An electrical voltage U is applied to this wire, so that electrical current flows through the wire. The flowing current heats the heating segment, and the heated detector heating segment releases thermal energy. The thermal energy released causes a combustible target gas to be oxidized in the interior of the housing, of course, only when the area contains this target gas. Methane ($CH_4$) is a combustible target gas to be detected in one application. Due to the supply of thermal energy, methane reacts with oxygen, and water and carbon dioxide are formed. Consequently, $H_2O$ and $CO_2$ are formed from $CH_4$ and $O_2$.

Thermal energy is released in the interior of the housing during the oxidation of the target gas. This thermal energy acts on the detector and raises the temperature of the wire, through which current flows. This rise in temperature is correlated with the thermal energy released and hence with the concentration of the target gas in the interior of the housing. A gas detection device with such a detector is sometimes called "heat tone sensor".

The temperature change leads to a change in a property of the detector, which property is correlated with the detector temperature, for example, with the electrical resistance R of the wire of the detector, through which wire the current flows. The electrical resistance of many electrically conductive materials increases with increasing temperature of the material. The gas detection device measures a measurable variable, which is influenced by the property and hence by the temperature and which will hereinafter be called "detection variable." The detection variable is, for example, directly the temperature or a variable that is correlated with the electrical resistance, for example, the electrical voltage U applied to the detector or the current intensity I or the electrical power P absorbed by the detector. If another measurable variable, which likewise depends on the electrical resistance R, is maintained at a constant value, the detection variable is correlated with the sought concentration of the target gas. If, for example, the current intensity I of the current flowing through the detector is maintained at a constant value, the electrical voltage U applied to the detector is correlated with the electrical resistance, the electrical resistance is correlated with the temperature, the temperature is correlated with the target gas concentration, and the electrical voltage U is thus correlated with the target gas concentration being sought.

The electrical voltage U applied to the detector causes an electrical current to flow. The flowing current heats the detector heating segment to a working temperature, which is often between 400° C. and 500° C. However, this working temperature alone is not sufficient, as a rule, for oxidizing a combustible target gas in the housing. A higher working temperature is often undesirable because it could lead to a combustion or even to an explosion of combustible target gas, which is often undesirable, and, in addition, it would involve a higher consumption of energy.

In order to make it nevertheless possible to oxidize a combustible target gas despite a working temperature below 500° C., the detector comprises a catalytic material, which oxidizes the target gas in connection with the heated heating segment. A gas detection device with such a detector is therefore also called a "catalytic sensor."

In a frequently used embodiment, the detector heating segment is enclosed by an electrical insulation, for example, by a ceramic jacketing. This electrical insulation electrically insulates the detector heating segment and prevents, in particular, an undesired short-circuit. The electrical insulation is thermally conductive in order for the detector heating segment to be able to release thermal energy into the surrounding area and, conversely, for thermal energy from the surrounding area to be able to continue heating the heating segment. A coating consisting of a catalytic material is applied to this electrical insulation, or else a catalytic material is embedded into the electrical insulation. This catalytic coating comes into contact with the gas mixture in the housing and hence also with a combustible target gas. Such a detector is often called a "pellistor."

FIG. 1 shows as an example a detector 10 configured as a pellistor as well as schematically the conversion of methane ($C_4$) into $CO_2$ and $H_2O$. The detector 10 comprises
- a helically wound and electrically conductive wire 20, which acts as a heating segment and is manufactured, for example, from platinum,
- a ceramic jacketing 21, which encloses the heating segment 20 and has the shape of a solid sphere in the example being shown,
- a catalytic coating on the outer surface of the ceramic jacketing 21, which is indicated by circles in FIG. 1,
- a mounting plate 22 and
- electrical connections and mechanical brackets 36 for the wire 20.

For example, platinum or palladium or another metal or another alloy is used as the catalytic material. As an alternative or in addition to the catalytic coating, catalytic material 23 may also be embedded in the ceramic jacketing 21.

The solid sphere of the detector 10 has a porous surface with a catalytic coating 23 in a preferred embodiment. In one embodiment, this porous surface is manufactured as follows: The detector 10 with the porous surface, but without the catalytic coating, is provided. The catalytic coating 23 is applied to the porous surface. Thanks to this porous surface, the detector 10 has a larger surface compared to a smooth surface. Thanks to this larger surface, the detector 10 is capable of oxidizing combustible target gas better, especially because a larger quantity of target gas comes into contact with the catalytic material. A gas can reach deeper layers of the detector 10 thanks to the porous surface.

Many combustible target gases to be detected have a higher thermal conductivity than air. If a gas mixture containing a combustible target gas encloses the detector 10, this gas mixture therefore cools the detector 10 and therefore reduces the electrical resistance of this detector. If combustible target gas is present, two opposite effects act therefore on the detector 10:
- on the one hand, the thermal energy, which is released by the oxidation and raises the temperature of the detector, and
- on the other hand, the increased thermal conductivity, which removes thermal energy and thereby lowers the temperature of the detector 10.

The effect of the oxidation is several times higher, for example, 10 times higher, in a new detector 10 than is the effect of the increased thermal conductivity. This may change in the course of use, which will be described below.

However, the temperature of the detector 10 and hence also the detection variable are influenced not only by the released thermal energy, but also by ambient conditions in the area to be monitored, which also change the conditions in the interior of the housing, especially the ambient temperature and, in addition, the humidity of the air and the particles in the air. These ambient conditions may likewise influence the temperature and hence the detection variable, for example, because the thermal conductivity is changed in the area surrounding the detector 10. It is desired that, on the one hand, the gas detection device be capable of detecting a combustible target gas reliably despite varying ambient conditions and, on the other hand, that it generate only few false alarms, i.e., that it happen only rarely that it determines that a target gas is present even though no target gas has occurred in reality above a detection threshold, which is an incorrect result.

The gas detection device therefore compensates the effect of ambient conditions on the detection variable up to a certain degree by calculation. The gas detection device comprises for this purpose a compensator 11, in addition to the detector 10. The compensator 11 likewise comprises a wire with a heating segment. An electrical voltage U is also applied to the compensator 11, so that electrical current flows and the compensator heating segment is likewise heated. The compensator 11 is likewise exposed to the varying ambient conditions.

At least when the detector 10 is working satisfactorily, the compensator 11 oxidizes a combustible target gas in the interior of the housing of the gas detection device to a lesser extent or not at all.

FIG. 2 through FIG. 5 schematically show four alternative embodiments of how a gas detection device 100 with a catalytic detector 10 and with a compensator 11 may be configured. The compensator 11 comprises in all four embodiments, just like the detector 10, an electrically conducting wire with a heating segment and a thermal insulation around the heating segment. A housing 1 as well as an opening Ö are shown in FIG. 2 through FIG. 5. The interior of the housing 1 is in a fluidic connection through the opening b with an area B to be monitored. The housing 1 impermeable to fluid and is heat resistant, with the exception of the opening Ö.

Figure 2:
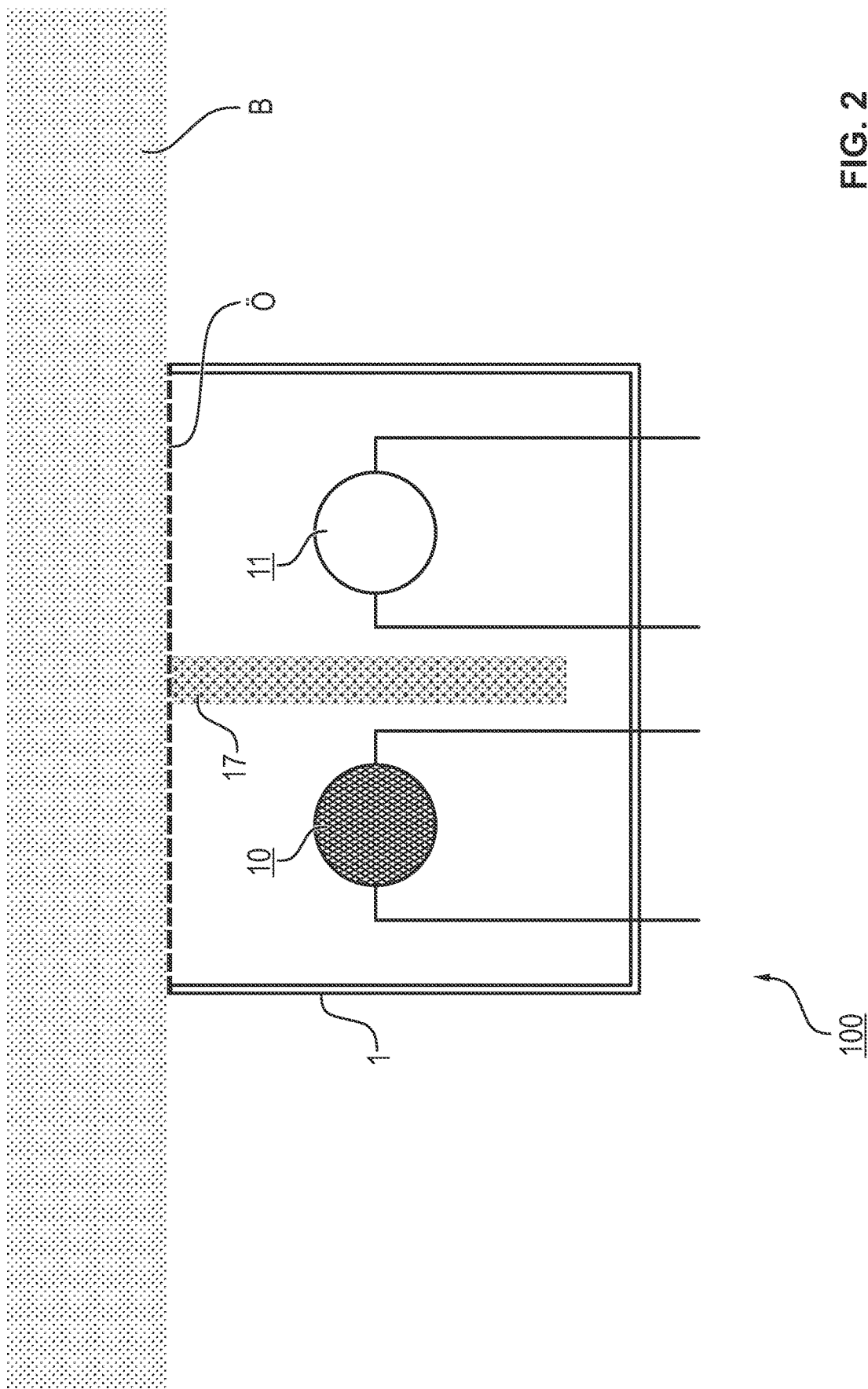
FIG. 2 is a schematic view showing a first possible embodiment of the gas detection device, in which the compensator is not capable of oxidizing a combustible target gas.

In the embodiment according to FIG. 2, the compensator 11 comprises no catalytic material, i.e., it is chemically inactive in respect to the target gas and is not capable of oxidizing the target gas. A gas mixture in area B flows through the opening Öboth to the detector 10 and to the compensator 11. An optional thermal barrier 17 insulates the compensator 11 thermally up to a certain degree from the detector 10. Thanks to the thermal barrier 17, the thermal energy, which is released during the oxidation of a combustible target gas, does not influence the compensator 11 at all or it does so to a markedly lesser extent only compared to the extent to which it influences the detector 10.

Figure 3:
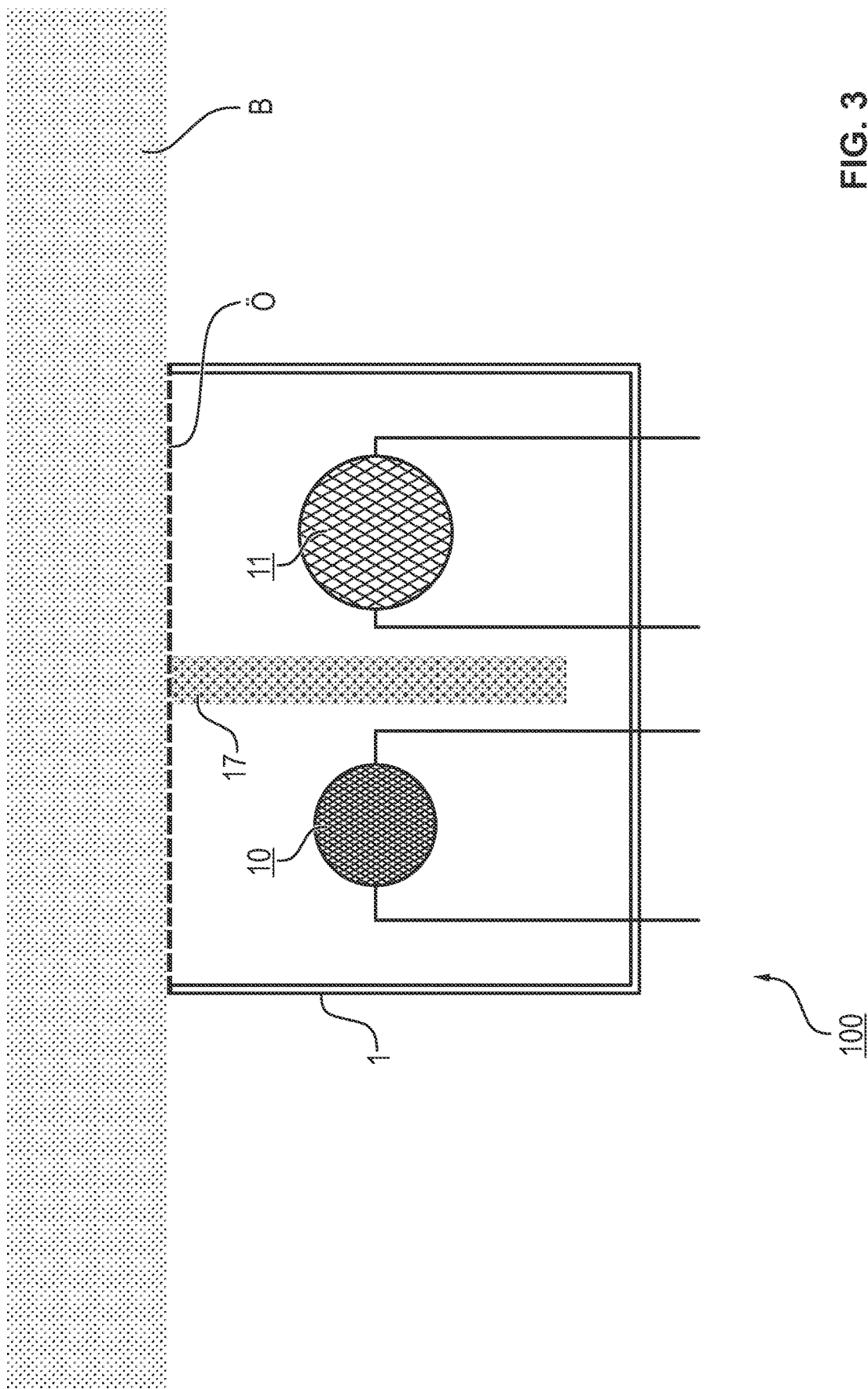
FIG. 3 is a schematic view showing a second possible embodiment of the gas detection device, in which the compensator is capable of oxidizing a combustible target gas to a lesser extent than is the detector.

In the embodiment according to FIG. 3, even though the compensator 11 comprises catalytic material, just like the detector 10, it is capable of oxidizing combustible target gas to a lesser extent than the detector 10. In one embodiment, the catalytic material of the compensator 11 has a lower surface density than the catalytic material of the detector 10. For example, the compensator 11 is larger than the detector 10, but it has the same quantity of catalytic material or even less catalytic material. The compensator 11 is capable of oxidizing less combustible target gas despite the larger surface because of the lower surface density. It is also possible that the surface of the compensator 11 is just as large as that of the detector 10. A thermal barrier 17 preferably separates the detector from the compensator 11 in the embodiment according to FIG. 3 as well.

In another embodiment of the configuration according to FIG. 3, the heating segment 20 of the detector 10 comprises more turns or has for other reasons a higher electrical resistance than the heating segment of the compensator 11, so that the heating segment 20 of the detector 10 is heated more intensely than the heating segment 30 of the compensator 11. It is also possible that a higher electrical voltage is applied to the detector 10 than to the compensator 11 or the intensity of the electrical current flowing through the detector is higher than the intensity of the electrical current flowing through the compensator 11.

Figure 4:
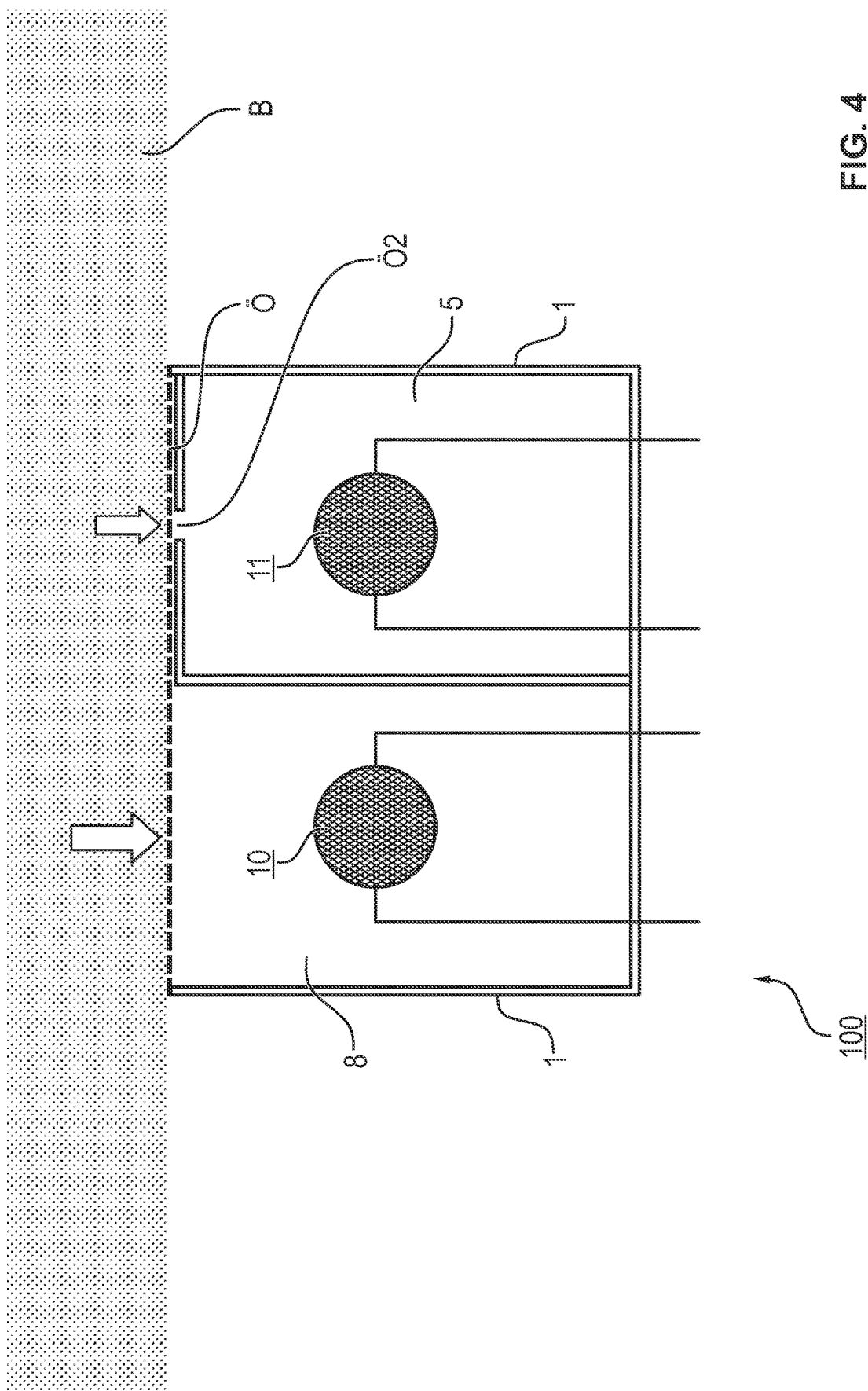
FIG. 4 is a schematic view showing a third possible embodiment of the gas detection device, in which the compensator, just like the detector, is capable of oxidizing a combustible target gas and is arranged in a compensator chamber, which is connected through an opening to the area to be monitored that is smaller than an opening connecting the detector to the area to be monitored.

The compensator 11 is arranged in the interior of the compensator chamber 5 in the embodiment according to FIG. 4. The compensator 11 is capable of oxidizing a combustible target gas, in one embodiment in exactly the same manner as the detector 10. The compensator chamber 5 is located in the interior of the housing 1 and encloses the compensator 11 in a fluid-tight manner, aside from the opening Ö2, which overlaps with the opening Ö in the example being shown. The area in the interior of the housing 1 that is located outside of the compensator chamber 5 will hereinafter be called "detector chamber" 8. The detector chamber 8 encloses the detector 10 and is in a fluidic connection with area B via the opening Ö. A gas mixture can flow from area B through the openings Ö and Ö2 into the compensator chamber 5. The area of the opening Ö2 equals at most one quarter and preferably at most 20% and especially preferably at most 10% of the area of the opening Ö. A smaller quantity of a gas mixture and hence also much less combustible target gas will reach the interior of the compensator chamber 5 from area B than the interior of the detector chamber 8.

Figure 5:
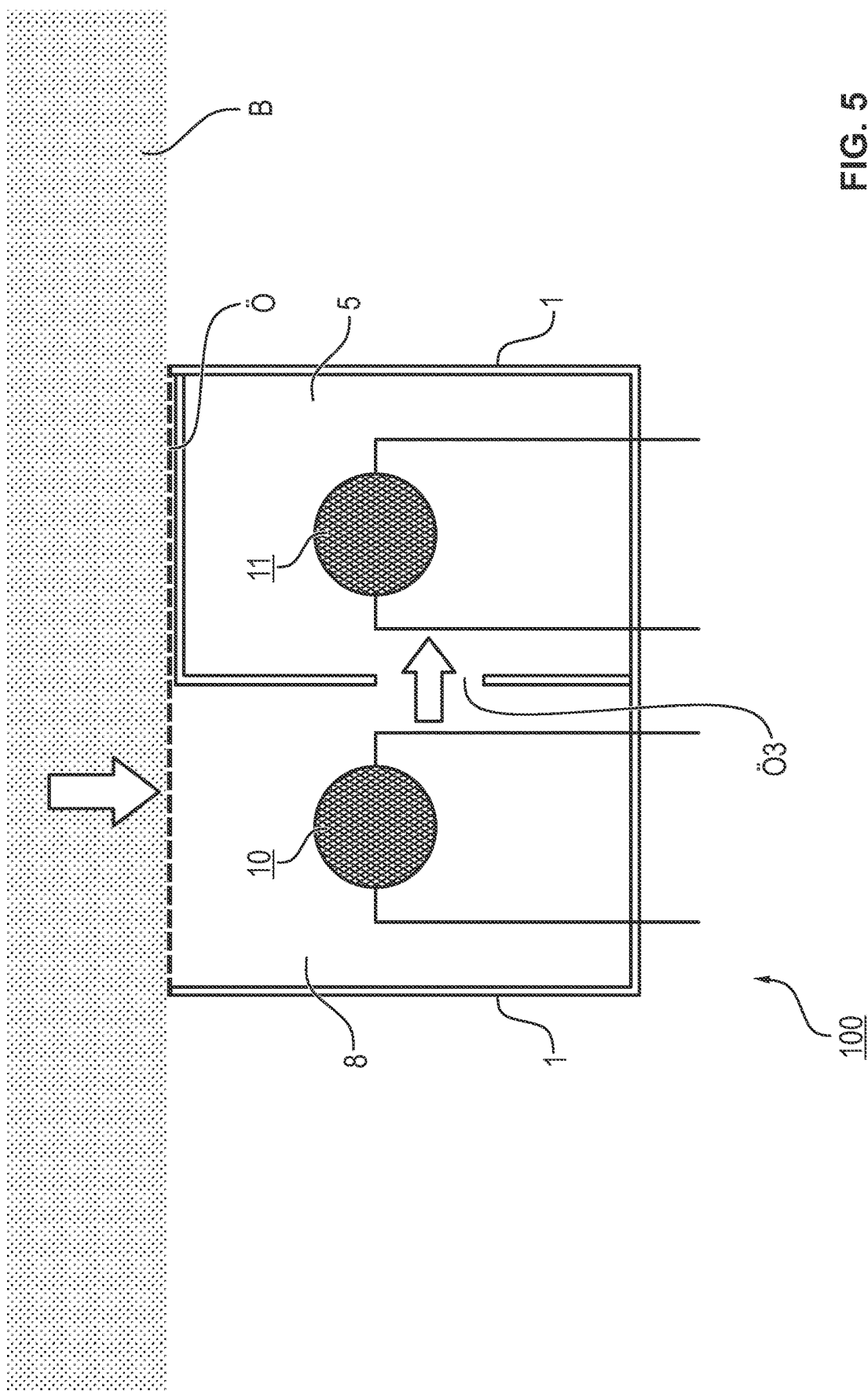
FIG. 5 is a schematic view showing a fourth possible embodiment of the gas detection device, in which the compensator, just like the detector, is capable of oxidizing a combustible target gas and is arranged in a compensator chamber, which is connected through a small opening to a detector chamber.

The compensator 11 is enclosed by a compensator chamber 5 in the embodiment according to FIG. 5 as well, and a detector chamber 8 is likewise formed around the detector 10. The compensator 11 is capable of oxidizing a combustible target gas. Contrary to the embodiment according to FIG. 4, a gas mixture cannot, however, diffuse from area B into the compensator chamber 5 because the compensator chamber 5 separates the compensator 11 from the opening Ö in a fluid-tight manner. The gas mixture can rather reach the compensator chamber 5 only from the detector chamber 8 through an opening Ö3. The area of the opening Ö3 is at most half that of the opening Ö, especially preferably at most a quarter, especially preferably at most 10% of the area of the opening Ö. Consequently, if the detector 10 oxidizes a combustible target gas in the compensator chamber 5 completely, no combustible target gas reaches the compensator chamber 5, even if area B contains this combustible target gas. A gas detection device having such a configuration is described, for example, in DE 10 2017 005 713 A1.

Figure 6:
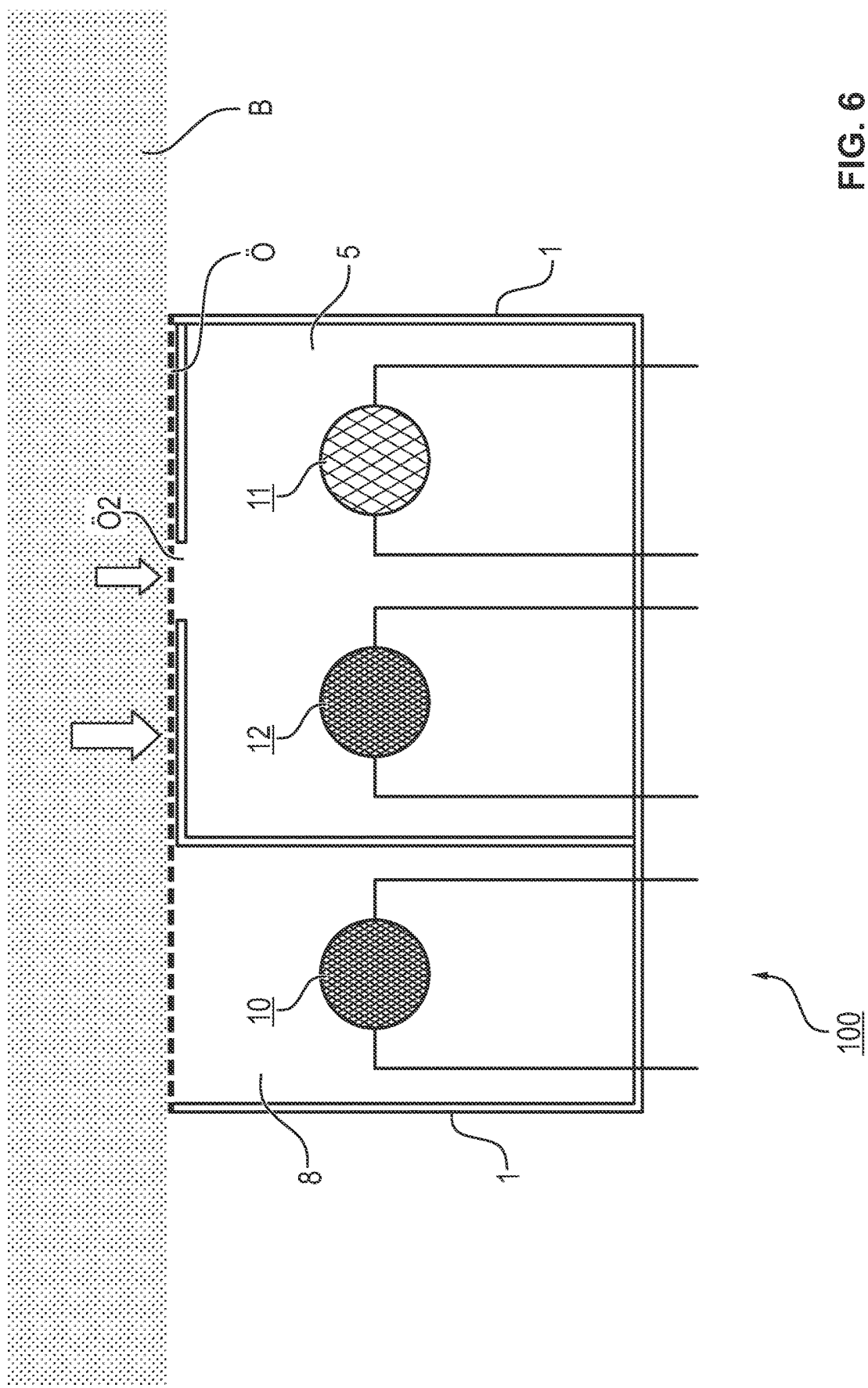
FIG. 6 is a schematic view showing a variant of the third embodiment according to FIG. 4, wherein an additional detector is additionally arranged in the compensator chamber and the compensator chamber is connected through a smaller opening to the area to be monitored.

FIG. 6 shows a variant of the embodiment according to FIG. 4. The compensator chamber 5 is connected through the smaller opening Ö2 with area B to be monitored. In addition to the compensator 11, an additional detector 12 is arranged in the compensator chamber 5. This additional detector 12 may have exactly the same configuration as the detector 10 in the detector chamber 8. The detectors 10, 12 are capable of oxidizing more target gas or of oxidizing target gas more rapidly than the compensator 11. Since the opening Ö2 is smaller than the opening Ö, only a smaller quantity of the gas mixture will reach the compensator 11 and the additional detector 12 compared to the quantity that reaches the detector chamber 8 through the opening b. The compensator 11 may also be arranged in the detector chamber 8 rather than in the compensator chamber 5.

Figure 7:
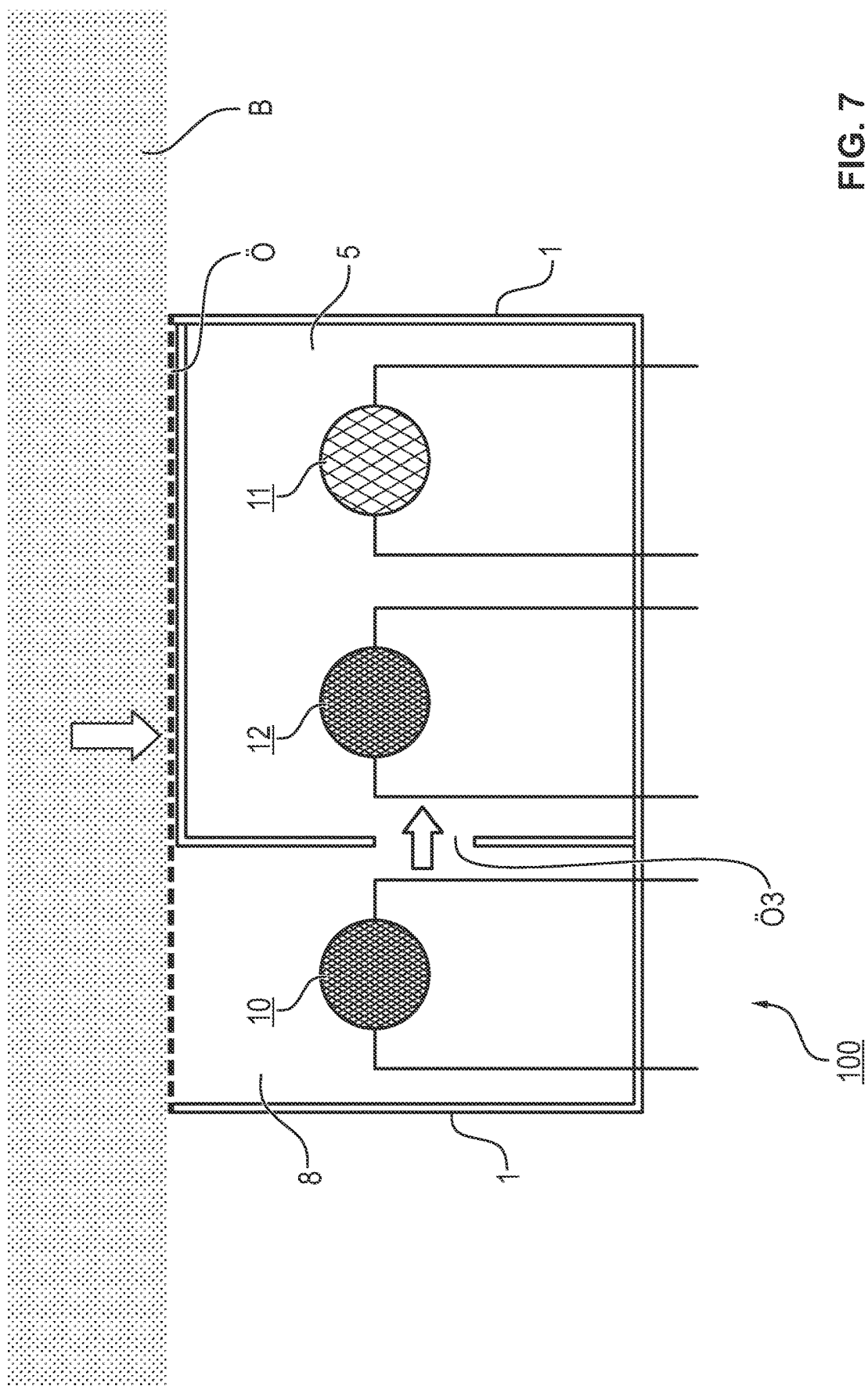
FIG. 7 is a schematic view showing a variant of the fourth embodiment according to FIG. 5, wherein an additional detector is additionally arranged in the compensator chamber and the compensator chamber is connected to the detector chamber.

FIG. 7 shows a variant of the embodiment according to FIG. 5. The compensator chamber 5 is not connected to area B to be monitored, but it is connected to the detector chamber 8 through a smaller opening Ö3. A gas mixture can reach only the compensator chamber 5 from area B when the gas mixture has flowed through the detector chamber 8 before. As long as the detector 10 is working satisfactorily, no combustible target gas will therefore reach the compensator chamber 5, because the combustible target gas was oxidized before by the detector 10 in the detector chamber 8. An additional detector 12 is, in turn, arranged in the compensator chamber 5. The compensator 11 may also be arranged in the detector chamber 8 rather than in the compensator chamber 5.

The gas detection device 100 measures in each embodiment the value that the detection variable assumes for the detector 10 and the value that it assumes for the compensator 11, and calculates the difference between these two values. How great the difference is between these two values when no target gas is present is known through a preceding adjustment or calibration. If the detector 10 and the compensator 11 are identical aside from the catalytic material, this difference is ideally zero. It is different from zero in practice.

This difference, determined in advance is used as an offset. The gas detection device 100 compensates the difference measured during the run time by the offset, for example, by subtracting the offset from the difference. The compensated difference determined in this manner is ideally equal to zero when no target gas is present in the area to be monitored. When the compensated difference is outside a tolerance range around zero, the gas detection device 100 determines automatically that a target gas above a detection threshold is present. The compensated difference is, in addition, an indicator of the concentration of the target gas being sought.

Figure 8:
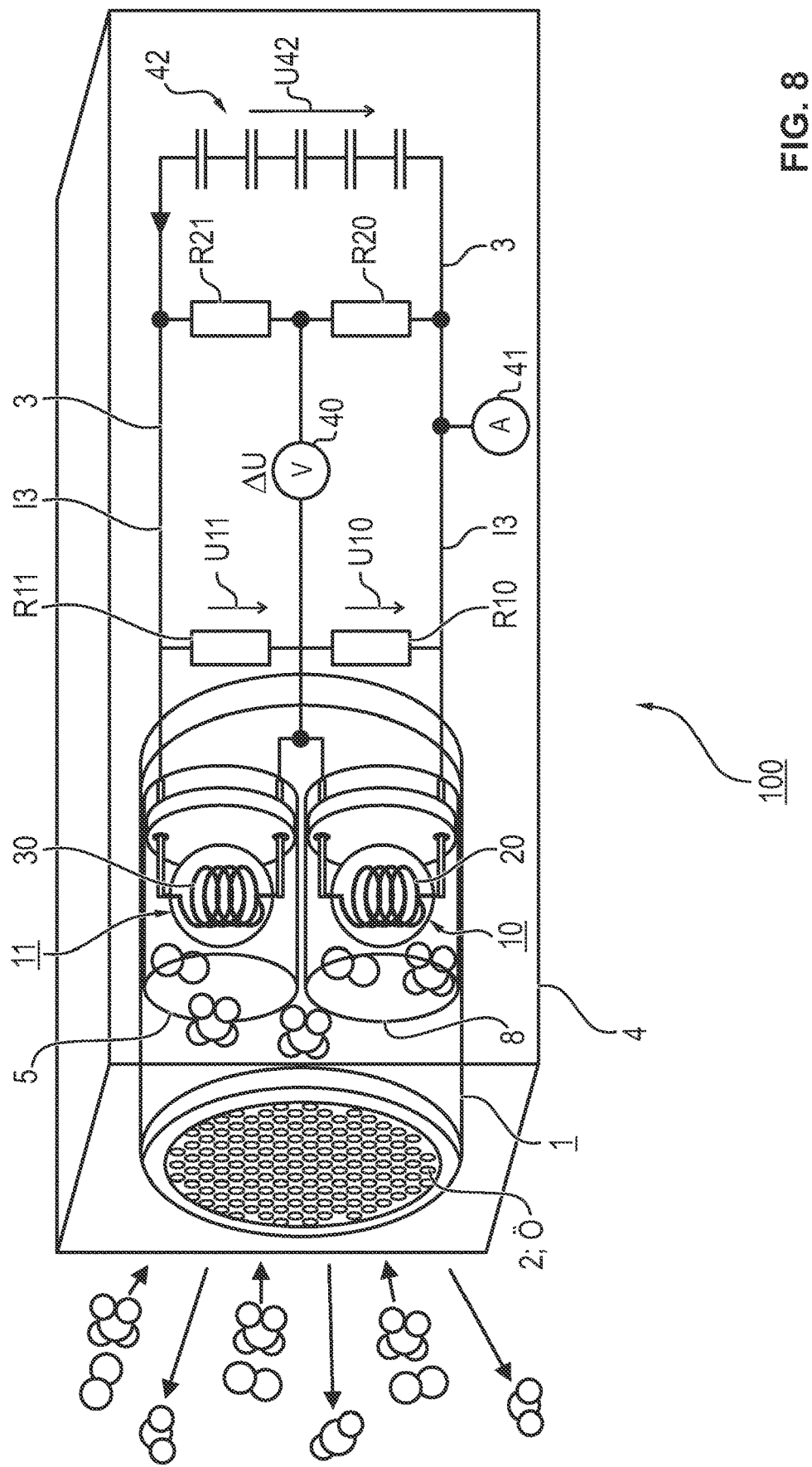
FIG. 8 is a schematic view showing a first embodiment of the gas detection device with a detector and with a compensator, both of which are configured as pellistors and are arranged in a Wheatstone bridge.

FIG. 8 shows an exemplary gas detection device 100 with the detector 10 and with the compensator 11, wherein the detector 10 comprises a heating segment 20 and the compensator 11 comprises a heating segment 30. In the example shown, the compensator 11 is likewise configured as a spherical pellistor and it preferably differs from the detector 10 in respect to one of the four embodiments, which was described in reference to FIG. 2 through FIG. 5.

In one embodiment, the gas detection device 100 is configured as a portable device, which a user can carry along when the user enters into an area in which a combustible target gas may occur. If the gas detection device 100 has detected a combustible target gas, it outputs an alarm in a form perceptible for a human being. The gas detection device 100 is configured as a stationary device in another embodiment.

The gas detection device 100 further comprises
- the compensator chamber 5 and the detector chamber 8, which are indicated schematically,
- a voltage source 42, for example, a set of rechargeable batteries,
- the stable inner housing 1, which accommodates the detector 10 and the compensator 11 and is in a fluidic connection with the surrounding area and hence with area B by means of the opening Ö,
- an outer housing 4, preferably one made of a solid plastic,
- a flame arrester 2 in the opening Ö, which prevents flames from escaping from the housing 1,
- optionally a thermal barrier 17, not shown, between the detector 10 and the compensator 11,
- two electrical resistors R20 and R21,
- an electrical line 3,
- a voltage sensor 40 and
- a current intensity sensor 41.

If the gas detection device 100 is configured as a stationary device, the gas detection device 100 may be connected to a stationary power supply network and the voltage source 42 may be omitted. It is also possible that the gas detection device is connected to both a stationary power supply source and a voltage source 42. This embodiment ensures that the gas detection device 100 can continue carrying out measurement when the stationary power supply network fails at times or supplies a fluctuating voltage.

The electrical resistor R20 is connected parallel to the detector 10, and the electrical resistor R21 is connected parallel to the compensator 11. FIG. 8 suggests
- the electrical resistance R10 of the detector 10,
- the electrical resistance R11 of the compensator 11,
- the voltage U42 of the voltage source 42,
- the electrical voltage U10 applied to the detector 10 and
- the electrical voltage U11 applied to the compensator 11.

It is noted that the term "electrical resistance" designates, on the one hand, an electrical property of a component, in this case, for example, the electrical resistance R10 of the detector 10, and, on the other hand, an electrical component, for example, the electrical resistor R20 connected parallel to the detector 10.

The respective electrical voltage U acts in the exemplary embodiment as the detection variable for both the detector 10 and the compensator 11. The components form a Wheatstone bridge in the example shown in FIG. 8. The detector 10 and the compensator 11 are connected in series. The electrical resistance of the voltage sensor 40 is high compared to the electrical resistances of the components 10, 11, R20, R21. In one embodiment, the voltage sensor 40 measures the so-called bridge voltage $\Delta U = (U10 - U11)/2$ directly. In another embodiment, the bridge voltage $\Delta U$ is derived from the individual electrical voltages U10 and U11.

Since the compensator 11 and the detector 10 are connected in series, the current intensity of the current flowing through the detector 10 is ideally equal to the current intensity of the current flowing through the compensator 11. This identical current intensity is designated by I3. The current intensity sensor 41 measures the current intensity I3. A signal-processing control device, not shown, seeks to maintain the current intensity I3 automatically at a constant value. The electrical voltage U is known to be proportional at constant current intensity to the electrical resistance R, and the electrical resistance R and hence also the electrical voltage U are correlated with the temperature.

The control device carries out a regulation, during which
 a predefined desired value I3_ref is the command variable for the current intensity I3,
 the actual current intensity I3, which is measured by the current intensity sensor 41, is the controlled variable, and
 an electrical voltage U is the manipulated variable, for example, the voltage U42 of the voltage source 42.

The thermal energy, which is released by the oxidation of a target gas, as well as varying ambient conditions act as disturbance variables. The regulation target is to make the deviation I3-I3_ref small, ideally equal to zero.

The electrical voltage U will be used below as an example as the detection variable and the current intensity I will be used as the additional variable, which likewise depends on the temperature and hence on the electrical resistance R. This additional variable 1 is regulated, and is preferably maintained at a constant value. The description can correspondingly also be extrapolated to any other suitable detector variable. In particular, the current intensity I or the electrical power P taken up may also be the detection variable, and the electrical voltage U applied may be the additional variable, which is regulated. It is also possible to use the electrical resistance or directly the temperature as the detection variable. The electrical resistance and hence the temperature are regulated in another embodiment, and the electrical voltage and the current intensity are measured. The voltage or the current intensity is then used as a detection variable.

The gas detection device 100 uses a predefined functional relationship, especially a characteristic, between the temperature and the electrical resistance, and this functional relationship is valid for a component (detector 10, compensator 11). In one embodiment, this functional relationship is predefined and stored in a memory of the gas detection device 100. In another embodiment, a predefined temperature of the component is set during a preceding adjustment, and the electrical resistance, which the component has at this temperature, is measured. This adjustment yields a reference point of the characteristic. This adjustment is carried out anew if needed. The gas detection device 100 uses this reference point as well as a stored, computer-analyzable calculation rule to determine the particular temperature for other values of the electrical resistance.

The gas detection device 100 is adjusted before the first use in one embodiment. How this initial adjustment is carried out will be explained below as an example and with reference to FIG. 8.

Even if no target gas is present, the electrical resistance R11 of the compensator 11 is not equal to the electrical resistance R10 of the detector 10. Therefore, at least one situation, in which no target gas is present, is established during the adjustment. A plurality of different situations, in which area B is free from combustible target gas, are preferably established, and different ambient conditions are set in this connection, for example, different ambient temperatures and air humidities. An offset is determined empirically for the detection variable, the offset occurring in the absence of target gas, i.e., there is a so-called zero voltage $\Delta U0$ here. The zero voltage $\Delta U0$ is set such that the difference from the bridge voltage $\Delta U$ and the zero voltage $\Delta U0$ is equal to zero or close to zero in a situation in which no target gas is present. For the bridge voltage: $\Delta U=(U10-U11)/2$.

This zero voltage U0 makes it possible to compensate the effects of different electrical resistances R10, R11 of the detector 10 and of the compensator 11 by calculation. The bridge voltage compensated by the offset $\Delta U0$ is designated by $\Delta U_{komp}$, i.e., $\Delta U_{komp}=\Delta U-\Delta U0$. As an alternative, the zero voltage $\Delta U0$ may also pertain to the difference between the two voltages U10 and U11 applied, i.e., it may be set such that $\Delta U-\Delta U0$ is ideally equal to zero in a state in which target gas is absent. Consequently, a zero value $\Delta U0$ is used in both embodiments for the difference between the values of the detection variable (here: the electrical voltage U applied) and it is used as an offset.

Two bridge voltages, namely, the above-described bridge voltage $\Delta U=(U10-U11)/2$, on the one hand, and an additional bridge voltage $\Delta U12=(U12-U11)/2$, on the other hand, are measured in the embodiments according to FIG. 6 and FIG. 7. The compensator 1 thus compensates both ambient conditions that act on the detector 10 and ambient conditions that act on the additional detector 12. The compensator 11 is used quasi twice. Two zero voltages are correspondingly calculated, namely, on the one hand, as was just described, the zero voltage $\Delta U0$ and, on the other hand, an additional zero voltage $\Delta U0,12$ as a difference between the two voltages U12 and U11 in a situation in which no target gas is present in the compensator chamber 5.

A signal-processing analysis unit of the gas detection device 100 checks whether the compensated difference $\Delta U_{komp}$ between the values of the detection variable U is within or outside of a predefined tolerance range around the zero value. If the difference is outside of this tolerance range, then a target gas is detected—more precisely, the event that the concentration of the target gas is above a detection threshold is detected. The analysis unit checks in the exemplary embodiment whether $(U10-U11)/2-\Delta U0$ or also $U10-U11-\Delta U0$ is within the tolerance range or not.

In the embodiments according to FIG. 6 and FIG. 7, the analysis unit checks whether at least one compensated bridge voltage $\Delta U_{komp}=\Delta U-\Delta U0$ or $\Delta U12_{komp}=\Delta U12-\Delta U0,12$ is within or outside of the tolerance range. It is possible that the two compensated bridge voltages are compared with the same tolerance range. In a different embodiment, the additional compensated bridge voltage $\Delta U12_{komp}$ is compared with a narrower tolerance range in order to take into account the circumstance that less gas mixture and hence less combustible target gas reaches the compensator chamber 5 and hence the additional detector 12 through the openings Ö2 and Ö3 compared to the quantity reaching the compensator chamber 8 and hence the detector 10 through the opening Ö. It is also possible that the analysis unit checks whether a weighted aggregation of the two compensated bridge voltages is within or outside of a tolerance range.

In one embodiment, the gas detection device 100 is configured to measure the concentration Con of a combustible target gas in area B to be monitored. A functional relationship F is preferably determined empirically between the compensated difference $\Delta U_{komp}$ and the sought concentration Con of the combustible target gas, i.e., $\Delta U_{komp}=F(Con)$, during the adjustment or also during a calibration.

Gas mixtures with different known concentration values con of the target gas are prepared for this purpose and fed to the gas detection device 100, and the respective resulting compensated bridge voltage $\Delta U_{komp}(\text{con})$ is determined for each concentration value produced. The functional summary is stored. This adjustment is preferably carried out repeatedly, for example, at regular predefined time intervals.

The concentration Con sought is calculated during the use according to the calculation rule $\text{Con}=\beta*F^{-1}(\Delta U_{komp})$. In the simplest case: $\text{Con}=\alpha*\beta*\Delta U_{komp}$ with an empirically determined correlation factor $\alpha$ and with a likewise empirically determined correction factor $\beta$. Both factors $\alpha$, $\beta$ will be explained bellow.

Figure 9:
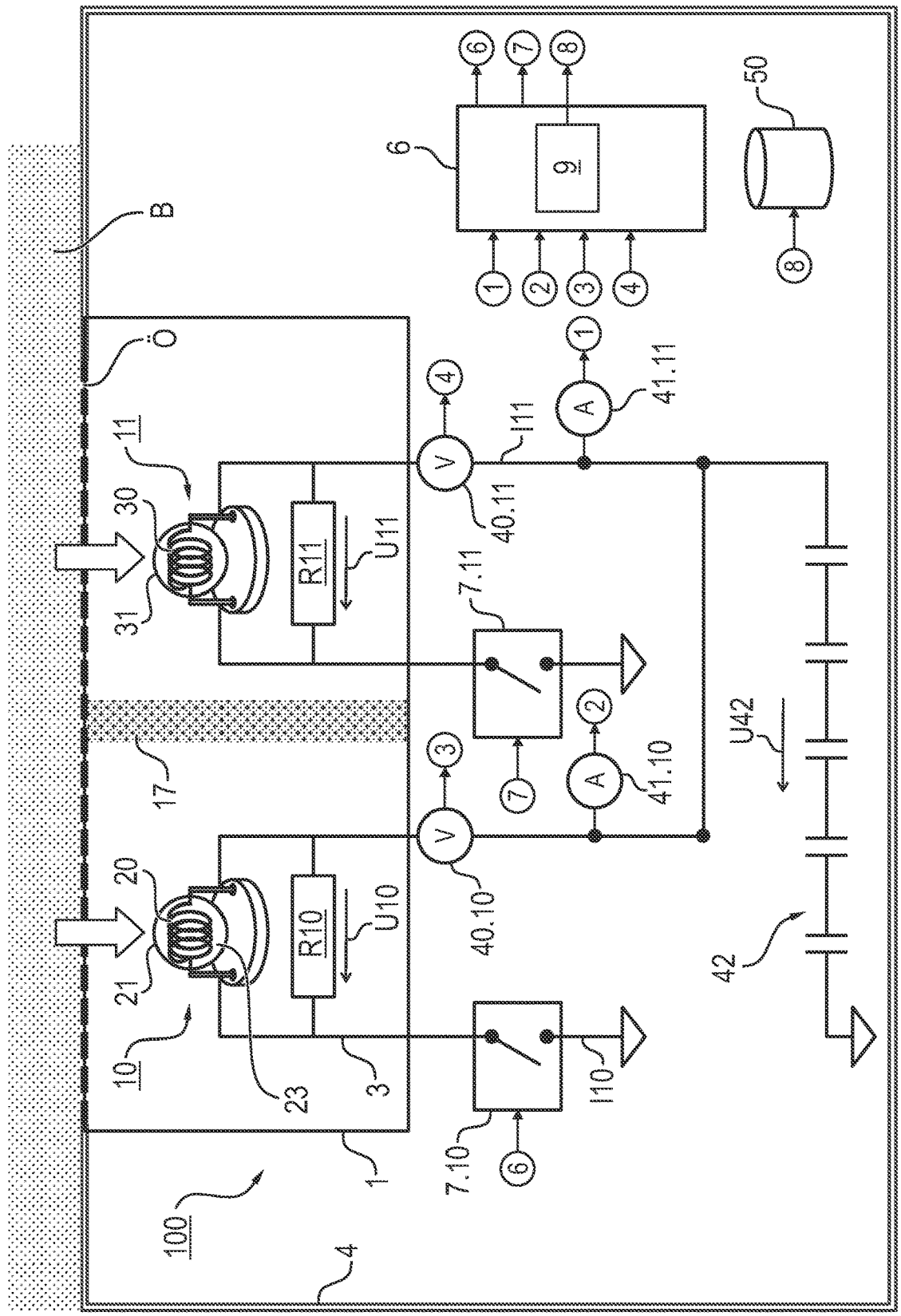
FIG. 9 is a schematic view showing a second embodiment of the gas detection device with a detector and with a compensator, both of which are configured as pellistors, wherein different current intensities can flow through the detector and through the compensator.

FIG. 9 shows a second embodiment of the gas detection device 100. Identical reference numbers have the same meanings as in FIG. 8. The gas detection device 100 according to FIG. 9 comprises
- the detector 10 with the heating segment 20, with the ceramic jacketing 21 and with the coating 23 consisting of a catalytic material,
- the compensator 11 with a heating segment 30 and with a ceramic jacketing 31 and optionally likewise catalytic material,
- the voltage source 42.
- two switches 7.10 and 7.11,
- two voltage sensors 40.10 and 40.11,
- two current intensity sensors 41.10 and 41.11,
- the electrical resistors R20 and R21,
- a signal-processing control device 6 with an analysis unit 9.
- a thermal barrier 17 between the detector 10 and the compensator 11,
- the outer housing 4 and
- the stable inner housing 1 with the opening.

Furthermore, the area B to be monitored as well as arrows, which illustrate how a gas mixture flows through the opening Ö into the interior of the housing 1, are shown. The embodiment according to FIG. 9 may be combined with each of the alternative embodiments according to FIG. 2 through FIG. 5 and, after a corresponding expansion, also with the embodiments according to FIG. 6 and FIG. 7. For example, the compensator 11 has no catalytic material, cf. FIG. 2. Or else, the compensator 11 has catalytic material with a lower surface density, cf. FIG. 3, or else it is heated less intensely by the electrical voltage applied, or else a compensator chamber 5 encloses the compensator 11 in a fluid-tight manner with the exception of an opening Ö2 towards area B, cf. FIG. 4 and FIG. 6, or with the exception of an opening Ö3 towards the detector chamber 8, cf. FIG. 5 and FIG. 7. The compensator chamber 5 and the detector chamber 8 are omitted in FIG. 9.

The current intensity I10 of the current flowing through the detector 10 may differ in the exemplary embodiment according to FIG. 9 from the current flowing through the compensator 1I. The current intensity sensor 41.10 measures the current intensity I10 and the current intensity sensor 41.11 measures the current intensity I11. The voltage sensor 40.10 measures the electrical voltage U10 applied to the detector 10, and the voltage sensor 40.11 measures the electrical voltage U11 applied to the detector 10. The values that have been measured by the sensors 40.10, 40.11, 41.10 and 41.11 are transmitted to the control device 6.

The control device 6 carries out a respective regulation in a detector control circuit and a regulation in a compensator control circuit. The regulation target in the detector control circuit is to maintain the current intensity I10 of the current flowing through the detector 10 at a predefined reference value I10_ref. The control device 6 changes, for example, the electrical voltage U10 applied to the detector by suitable adjusting actions in order to reduce a deviation between the reference value I10_ref and the measured current intensity I10. The regulation target in the compensator control circuit is correspondingly to maintain the current intensity I11 of the current flowing through the compensator 11 at a predefined reference value I11_ref. The control device 6 changes the electrical voltage U11 applied to the compensator 11 as needed.

Since the current intensity I10, I11 is maintained at a constant value, the electrical voltage U10, U11 is a linear function of the electrical resistance R10, R11. The analysis unit 9 determines, in turn, the difference $\Delta U-\Delta U0$ and checks whether this difference is within or outside of a predefined tolerance range around the zero point, wherein $\Delta 0$ is a zero voltage determined in advance. It optionally calculates the concentration of a combustible target gas.

In order to save electrical energy, the control device 6 causes in the exemplary embodiment a pulsed voltage to be applied to the detector 10 and at the compensator 11 instead of an electrical voltage being applied continuously. The control device 6 actuates the two switches 7.10 and 7.11 with the goal of pulsing the electrical voltage U10 and U11 applied to the detector 10 and at the compensator 11. The pulse rate of the electrical voltage U10 applied to the detector 10 can preferably be set and changed independently from the pulse rate and the pulse duration of the electrical voltage U11 applied to the compensator 11.

The present invention offers a solution for the problem that the detector 10 changes in the course of time. A frequently occurring change is also called poisoning and it results especially from the fact that siloxanes, hydrogen sulfide and other harmful gases reach the heated surface of the detector 10, undergo chemical changes and cause deposits to be formed on the surface of the detector 10. In addition, the oxidation of target gas can cause partially oxidized material to be deposited on the surface 21 of the detector 10 (coking). Based on at least one of these two possible developments, the detector 10 is capable of oxidizing an increasingly smaller quantity of target gas over the course of time. As a result, less thermal energy is released at equal concentration of a combustible target gas, less thermal energy heats the heating segment 20, and the temperature of the detector 10 rises less intensely. When less thermal energy is released, the detection variable U10 will increase less intensely compared to a state in which no target gas is present. Depending on the embodiment of the gas detection device 100, the compensator 11 is compromised less or not at all by the fact that oxidized material is deposited or harmful gases act on the surface.

The gradual change of the detector 10 causes the same value con for the concentration Con of the target gas to over time lead to an increasingly lower detector temperature and hence to an increasingly lower value that the detection variable for the detector 10 assumes. For example, the electrical voltage U10 applied to the detector decreases steadily over time at equal target gas concentration. The compensated bridge voltage $\Delta U_{komp}$ also decreases therefore steadily at equal value for the target gas concentration. This process is sometimes also called a "poisoning" of the gas detection device.

FIG. 10 schematically illustrates a gradual poisoning, wherein the gas detection device 100 has the configuration according to FIG. 5. A combustible target gas, in this example methane ($CH_4$), can reach the compensator chamber 5 only through the detector chamber 8 and the opening Ö3. The time t is plotted on the x axis of the diagrams, and the temperature Temp is plotted on the y axis. The temperature of the detector 10 is designated by Temp_10 and that of the compensator 11 is designated by Temp_11.

Neither the detector 10 nor the compensator 11 is poisoned in FIG. 10 *a*). The temperature Temp_10 of the detector 10 is markedly higher than the temperature Temp_11 of the compensator 11.

The detector 10 is already poisoned slightly in FIG. 10 *b*). The temperature Temp_10 of the detector 10 is slightly lower than in FIG. 10 *a*). The detector 10 oxidizes all target gas in the detector chamber 8 in this situation as well, so that no combustible target gas reaches the compensator chamber 5.

The detector 10 is poisoned to a greater extent in FIG. 10 *c*) and is incapable of oxidizing all the combustible target gas in the detector chamber 8. The temperature Temp_10 of the detector 10 is markedly lower than in FIG. 10 *a*). Combustible target gas reaches the compensator chamber 5 through the opening Ö3 and is oxidized there by the compensator 11. As a result, the temperature Temp_11 of the compensator 11 rises slightly compared to FIG. 10 *a*) and FIG. 10 *b*).

The detector 10 is poisoned in FIG. 10 *d*) to such a great extent that it cannot practically oxidize any more target gas at all. The temperature Temp_10 of the detector 10 depends essentially only on the ambient temperature but not on the concentration of the target gas. Combustible target gas is not oxidized in the detector chamber 8, but it enters through the opening Ö3 into the compensator chamber 5 and is oxidized by the compensator 11 there. As a result, the temperature Temp_11 of the compensator 11 rises substantially.

One consequence of the fact that the detector 10 gradually becomes poisoned is as follows: The measured bridge voltage, i.e., the difference $\Delta U=(U10-U11)/2$, and also the compensated difference $\Delta U_{komp}=\Delta U-\Delta U0$, become steadily lower. Without a countermeasure, the compensated difference $\Delta U_{komp}$ can therefore be within the above-mentioned tolerance range around zero, even though a target gas is present in area B to be monitored. The gas detection device 100 is not capable of detecting this combustible target gas. It will be described below how this undesired situation is automatically detected and optionally avoided.

As was already described, a zero value, namely, a value that the difference between the values of the detection variable assumes when no target gas is present, is predefined for the detection variable. The zero voltage $\Delta U0$ is predefined in the embodiment with the electrical voltage U as the detection variable such that $\Delta U-U0$ becomes equal to zero or is at least within a tolerance range around zero when no target gas is present.

According to a preferred embodiment of the present invention, a detector zero value, i.e., a zero value of the detection variable for the detector 10, and a compensator zero value, which is a zero value of the detection variable for the compensator 11, are additionally predefined. A detector zero voltage U0,10 and a compensator zero voltage U0,11 are consequently predefined in the case of the electrical voltage U as the detection variable. These two zero values U0,10 and U0,11 are determined during an adjustment. At least one gas mixture, which contains no combustible target gas, is fed for this purpose to the gas detection device 100. The values which the detection variable assumes in this case for the detector 10 and for the compensator 11 are measured. Consequently, two values are measured, i.e., the two zero voltages U0,10 and U0,11 in the case of the electrical voltage U.

An additional detector zero voltage, which is designated by U0,12, is determined with an additional detector 12 in the embodiment according to FIG. 6 and FIG. 7. It is consequently determined what voltage is applied to the additional detector 12 when no target gas is present in the compensator chamber 5. A detector zero value of another physical variable is correspondingly measured in case of a detection variable other than the electrical voltage.

The analysis unit 9 determines a respective value each for the electrical voltage U10 applied to the detector 10 and for the electrical voltage U11 applied to the compensator 11 during the use. In the embodiment according to FIG. 8, the analysis unit 9 derives the two values for the voltages U10, U11, for example, from measured values of the voltage sensor 40 and of the voltage U42 of the voltage source 42, since U42=U10+U11 is true, except for voltage losses. The voltage sensor 40 measures the bridge voltage (U10−U11)/2. In the embodiment according to FIG. 9, the two voltage sensors 40.10 and 40.11 measure the two voltages U10 and U11 directly. A third voltage sensor (not shown) measures the electrical voltage U12 that is applied to the additional detector 12 in the embodiment according to FIG. 6 and FIG. 7.

A difference between the measured value and the zero value of the detection variable is different both for the detector 10 and for the compensator 11. If the electrical voltage U is used as the detection variable, the two differences $U10_{komp}=U10-U0,10$ and $U11_{komp}=U11-U0,11$ are consequently calculated. The difference $U10_{komp}$ and $U11_{komp}$ is designated below as "compensated value" of the detection variable U. Each compensated value is ideally equal to zero if no combustible target gas is present. Each compensated value depends in practice not only on the concentration of a combustible target gas, but also on ambient conditions, especially on the ambient temperature and the humidity of the air. If an additional detector 12 is used, an additional compensated value of the detection variable U, namely, $U12_{komp}=U12-U0,12$, is calculated.

The analysis unit calculates according to the present invention a quality parameter Q for the gas detection device 100, doing so depending on the two compensated values for the detection variable. The analysis unit 9 preferably calculates the quality parameter Q each time repeatedly when it has detected a combustible target gas.

It will first be described below as an example how the quality parameter Q is calculated for a gas detection device 100, which is configured as described with reference to FIG. 5. What effects an increasing poisoning of the detector 10 has was described in reference to FIG. 10. The increasing poisoning leads to a reduction of the temperature Temp_10 of the detector 10 and hence also of the compensated electrical voltage $U10_{komp}$ which is applied to the detector 10 and is used as a detection variable. The temperature Temp_11 of the compensator 11 and hence also the compensated electrical voltage $U11_{komp}$ applied to the compensator 11 and used as a detection variable do, by contrast, rise as a consequence of the poisoning of the detector 10 since more combustible target gas reaches the compensator chamber 5.

The quality parameter Q is calculated according to the present invention such that the quality parameter Q decreases with decreasing compensated value of the detection variable for the detector 10 and with increasing compensated value of the detection variable for the compensator 11. For example, the quality parameter Q is calculated as a quotient of these two compensated values, i.e., according to the calculation rule $Q=U10_{komp}/U11_{komp}$ in the case of the electrical voltage U as the detection variable. An alternative is to calculate as the quality parameter Q the difference between these two compensated values. Different combinations of these two embodiments are possible as well.

In one embodiment, the compensator 11 is incapable of oxidizing a combustible target gas, cf. FIG. 2. However, a combustible target gas has, as a rule, a higher thermal conductivity than air, so that the compensator is cooled by the combustible target gas. A combustible target gas reduces in this case the electrical resistance and hence also the electrical voltage U11. In this case, $U11_{komp}=U11-U0,11$ is negative. The value $|U11_{komp}|$ of $U11_{komp}$ is used in this embodiment. The quality parameter Q decreases with a decrease in the compensated value of the detection variable for the detector 10 and with an increase in the value of the compensated value of the detection variable for the compensator 11.

The higher the quality parameter Q, the more reliable the gas detection device 100 currently is. In other words, the lower the quality parameter Q is, the more intensely the gas detection device 100 is currently poisoned. FIG. 10 e) shows as an example how the quality parameter Q decreases over time based on the increasing poisoning of the detector 10.

As was already mentioned, a calculation rule, which leads to a decrease in the quality parameter Q with the decrease in the compensated value of the detection variable for the detector 10 and with the increase in the compensated value of the detection variable for the compensator 11, is used for the calculation of the quality parameter Q. The increasing poisoning reduces the compensated value for the detector 10, e.g., $U10_{komp}$, and increases the compensated value, e.g., $U11_{komp}$, for the compensator 11. The increasing poisoning consequently leads to a rapid reduction of the quality parameter Q. If the quotient is used as the quality parameter Q, the numerator of this quotient becomes steadily smaller and the denominator becomes steadily greater.

The quality parameter Q is calculated in the embodiment according to FIG. 6 and FIG. 7 such that the quality parameter Q decreases
  with decreasing compensated value of the detection variable for the detector 10 and/or with decreasing compensated value of the detection variable for the additional detector 12 and
  with increasing compensated value of the detection variable for the compensator 11.

Two calculation rules, which yield two individual quality parameters Q10 and Q12, are used in one embodiment. The first individual quality parameter Q10 depends, just like the quality parameter Q just described, only on the detector 10 and on the compensator 11 and it decreases with decreasing compensated value of the detection variable for the detector 10 and with increasing compensated value of the detection variable for the compensator 11. The first individual quality parameter Q10 is, for example, the quotient $U10_{komp}/U11_{komp}$. The second individual quality parameter Q12 depends only on the additional detector 12 and on the compensator 11 and it decreases with decreasing compensated value of the detection variable for the additional detector 12 and with increasing compensated value of the detection variable for the compensator 11. The second individual quality parameter Q12 is, for example, the quotient $U12_{komp}/U11_{komp}$, or else this quotient, multiplied by a factor, yields the second individual quality parameter Q12, in which case the factor compensates the fact that less gas mixture and hence less combustible target gas reaches the compensator chamber 5 containing the additional detector 12. For example, the higher of the two individual quality parameters Q10 and Q12 is used as the quality parameter Q.

This rule will be explained below with reference to FIG. 7. In case of an intact detector 10, combustible target gas is oxidized in the detector chamber 8 and no combustible target gas at all or only a small quantity of combustible target gas reaches the compensator chamber 5 through the opening Ö3. The individual quality parameter Q10 assumes a high value, and the individual quality parameter Q12 has no influence on the quality parameter Q. The gas detection device 100 is capable of detecting the combustible target gas by means of the detector 10. The individual quality parameter Q10 becomes lower as the poisoning of the detector 10 increases. Since the detector 10 is capable of oxidizing less combustible target gas, more combustible target gas reaches the compensator chamber 5 and is oxidized there by the additional detector 12. The individual quality parameter Q10 will therefore rise steadily. As long as at least the additional detector 12 is capable of oxidizing a combustible target gas to a sufficient extent and the combustible target gas is heated by the oxidation, the gas detection device 100 according to FIG. 7 is still capable of detecting the combustible target gas.

As was mentioned already, many combustible target gases have a higher thermal conductivity than air. Such a combustible target gas therefore cools both the detector 10 and the compensator 11. However, this cooling affects the compensated values for the detector 10 and for the compensator 11 more or less in the same manner. A varying ambient condition also affects the compensated values for the detector 10 and for the compensator 11 in approximately the same manner. The quality parameter Q is therefore relatively insensitive to the effects of the cooling and of the varying ambient conditions.

An alarm is preferably outputted in a form perceptible for a human being when the quality parameter Q drops below a predefined minimal threshold and/or when the quality parameter Q decreases more rapidly than a predefined change threshold, or else a message is transmitted in this case to a receiver located at a distance.

Figure 11:
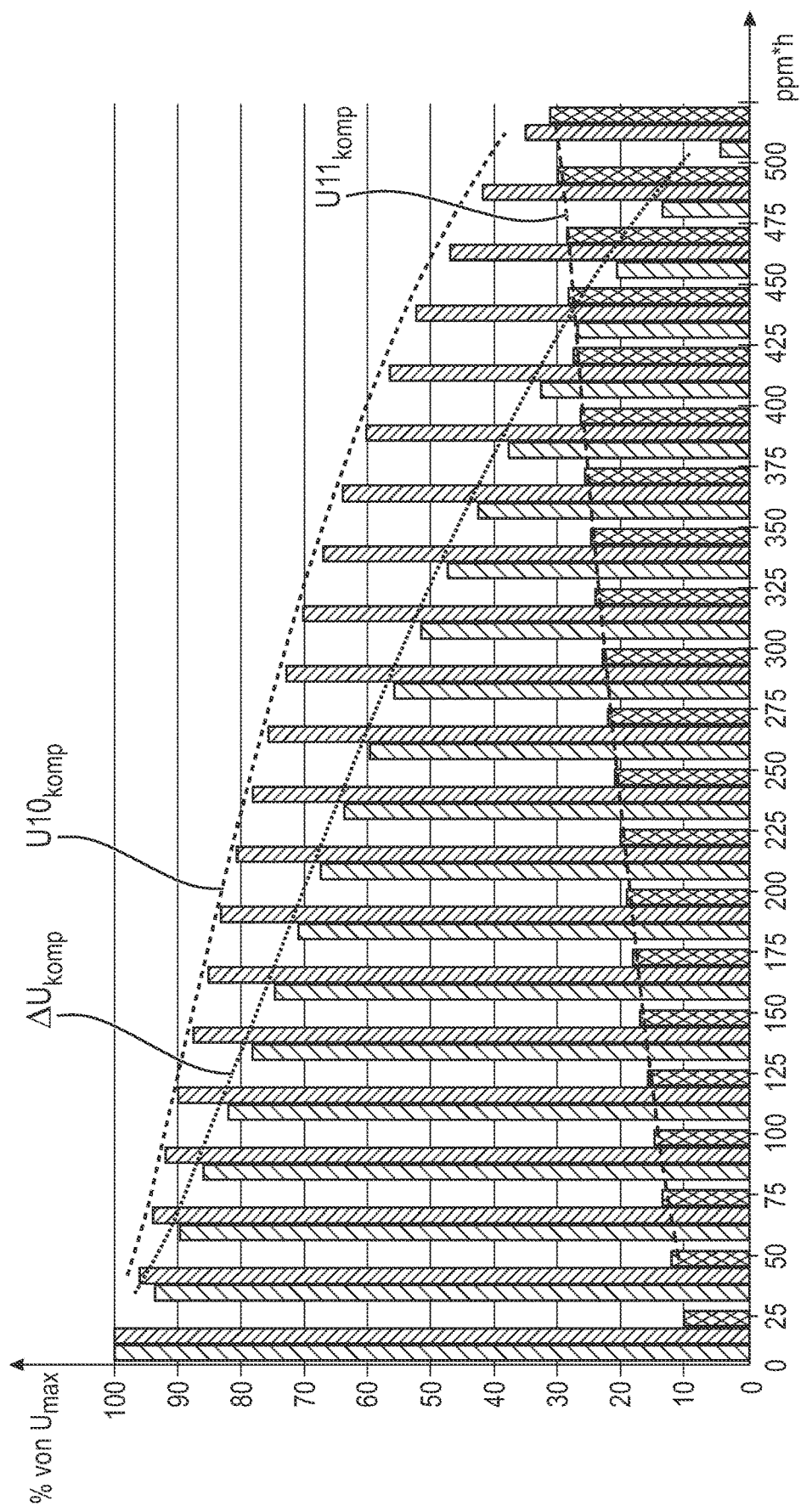
FIG. 11 is a graph showing, as an example, effects of an increasing poisoning of the detector based on a loading by a combustible target gas.

FIG. 11 shows as an example how detection variables change when the detector 10 of a gas detection device 100 according to FIG. 5 is gradually being poisoned. As was explained with reference to FIG. 10, the temperature Temp_10 of the detector 10 gradually decreases based on the poisoning of the detector 10, and the temperature Temp_11 of the compensator gradually increases.

On the x axis of FIG. 11 is plotted an indicator of the loading of the detector 10 with a harmful gas, which can enter into the inner housing 1 as a part of the gas mixture to be analyzed and then leads to deposits on the surface of the heated detector 10. The loading parameter is, for example, the accumulated concentration in [ppm*h] of an exemplary harmful gas, hexamethyldisiloxane, which burns at the detector 10 and produces silicon dioxide as a solid deposit on the surface. The respective compensated value of the detector variable U is plotted on the y axis as a percentage of the compensated value in case of a gas detection device 100 that has not yet been poisoned. It can be seen that the compensated value $U10_{komp}$ for the detector 10 drops from an initial value of 100% to below 40%, the compensated value $U11_{komp}$ for the compensator 11 increases from 10% to 30% and the compensated difference $\Delta U_{komp}$ therefore drops from 100% to less than 10%. The measured values in FIG. 11 were obtained, for example, in an experiment in which the current loading with harmful gases is measured continuously.

Figure 12:
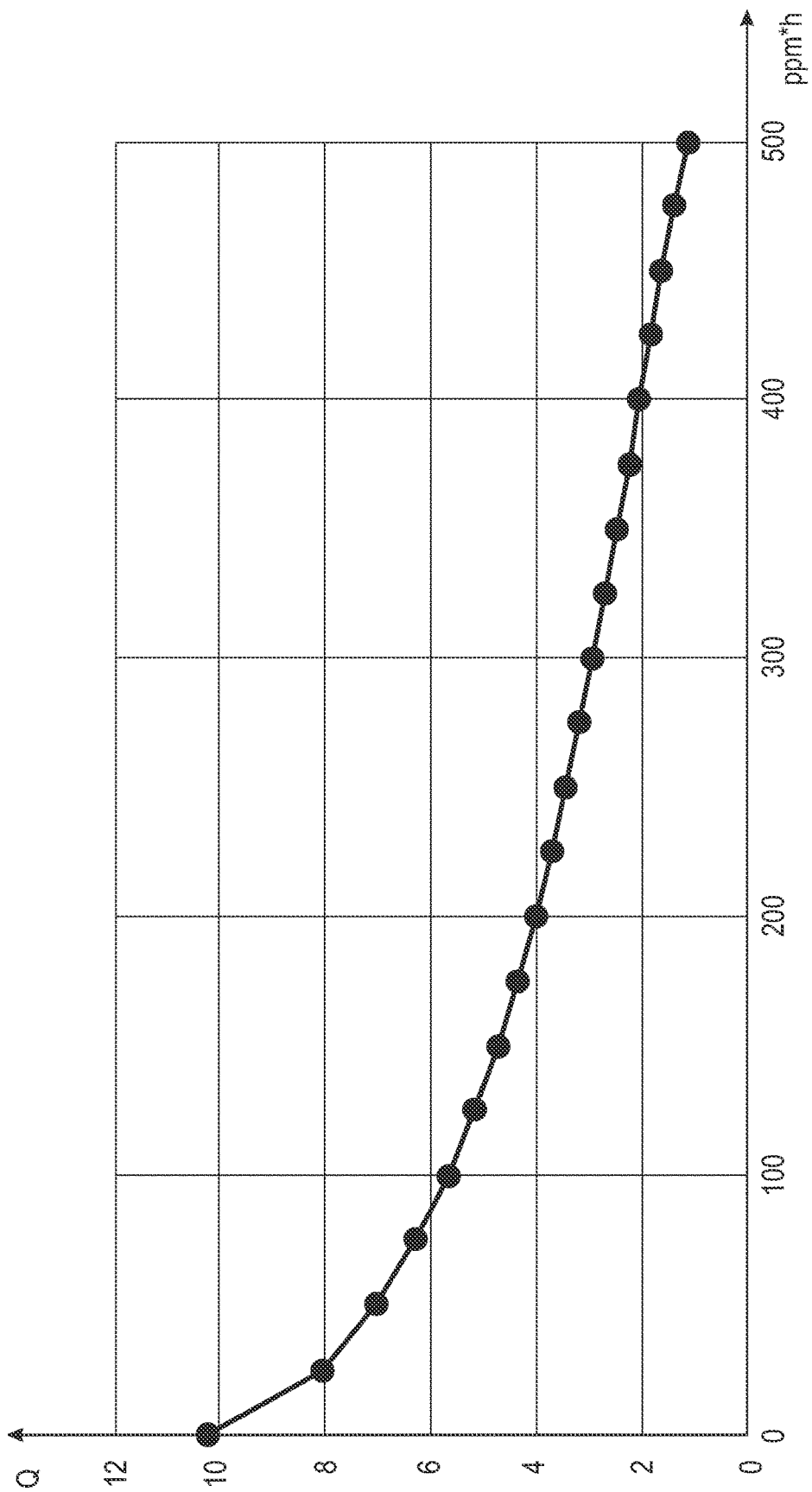
FIG. 12 is a graph showing an exemplary decrease in the quality parameter G based on a poisoning of the detector.

The quality parameter $Q=U10_{komp}/U11_{komp}$ correspondingly drops even more strongly. FIG. 12 shows as an example the decreasing quality parameter Q. The accumulated concentration in [ppm*h] of a combustible target gas is plotted on the x axis, and the quality parameter Q is plotted on the y axis.

The increasing poisoning of the detector 10 then becomes noticeable in a reduced quality parameter Q when a combustible target gas is indeed present in area B and hence in the interior of the housing 1. As long as the detector 10 is not yet completely poisoned, both the increase in the detector temperature Temp_10 and the increase in the compensator temperature Temp_11, which are brought about by the oxidation of the target gas, increase with increasing concentration of the combustible target gas in the gas mixture. The increasing poisoning of the detector 10 therefore causes a reduction of the quality parameter Q at each sufficiently high concentration of the target gas. This effect is true for each gas detection device 100 in which both the detector 10 and the compensator 11 are capable of oxidizing a combustible target gas, especially for a gas detection device 100 that is configured as shown schematically in FIG. 3, FIG. 4 or FIG. 5. Even though the quantity of combustible target gas that can reach the surrounding area of the compensator 11 does not depend on the poisoning of the detector 10 in the case of the embodiment according to FIG. 3 or according to FIG. 4 because a gas mixture can flow directly from area B to the compensator 11 in these embodiments, the compensator 11 is capable of oxidizing less target gas at equal concentration of the target gas in these embodiments of the compensator 11 as well, and the compensator 11 is poisoned therefore more slowly than the detector 10, which likewise leads to a reduced quality parameter Q.

As long as the poisoning of the detector 10 is not yet too intense, the gas detection device 100 is still capable of detecting a combustible target gas despite the poisoning. Two approaches to increasing the reliability of the gas detection device 100 in case of increasing poisoning will be described below.

The gas detection device 100 preferably comprises a memory 50, cf. FIG. 9, in which the time course of the quality parameter Q is stored. Whenever the gas detection device 101 has detected combustible target gas, the current value of the quality parameter Q is calculated anew and stored in this memory 50. The stored values provide a time course of the quality parameter Q, for example, the quality parameter time course shown in FIG. 12. In addition, the respective measured concentration of the target gas is stored.

This embodiment makes it possible to estimate the current quality of the gas detection device 100 as a function of the previous time course of the quality parameter Q. For example, an instruction for checking the gas detection device 100 in time is outputted depending on the previous time course of the quality parameter Q.

In a preferred embodiment, the quality parameter Q is used, on the one hand, to generate an alarm in a form perceptible for a human being and/or to transmit a message to a receiver located at a spaced location when the gas detection device 100 does not operate sufficiently reliably any more. The alarm is generated and/or the message is transmitted when a target gas is detected and the quality parameter Q then currently calculated drops below a predefined quality threshold. The gas detection device 100 preferably automatically triggers the step of generating the alarm and/or transmitting the message.

The quality parameter Q is preferably used, in addition, to automatically adapt the gas detection device 100 to the increasing poisoning as long as the quality parameter Q is still above the quality threshold. The gas detection device 100 preferably carries out this adaptation automatically itself. As was already explained, the analysis unit 9 determines automatically that a target gas is present if the compensated difference between the two values, which the detection variable for the detector 10 and for the compensator 11 assumes, is outside of a predefined tolerance range around zero. In case of the applied electrical voltage U as the detection variable, a target gas is detected, for example, when $\Delta U_{komp}$ is outside of the tolerance range [−D, +D] or [0, +D] with a predefined tolerance value D.

In one embodiment, the gas detection device 100 changes this tolerance value D automatically depending on the quality parameter Q, doing so such that the lower the quality parameter Q, the lower is D and the narrower is therefore the tolerance range. Consequently, D=f(Q) with a function rising monotonically for Q, for example, $D=f(Q)=D_0*Q/Q_0$ with an initial tolerance value $D_0$ and with an initial quality parameter $Q_0$. The initial quality parameter $Q_0$ is, for example, 10 in the example shown in FIG. 12 and in FIG. 13. The tolerance value D decreases steadily with advancing poisoning of the gas detection device 100 and therefore with decreasing quality parameter Q.

As was already described, the gas detection device 100 is capable of determining in one embodiment the concentration Con of a target gas as a function of the compensated difference between the two values of the detection variable for the detector 10 and for the compensator 11. If the electrical voltage U is used as the detection variable, the gas detection device 100 uses for this the calculation rule $Con=F^{-1}(\Delta U_{komp})$, the relationship F having been determined empirically in advance. This relationship F is preferably valid for a single copy of a gas detection device 100 and may differ from one copy to the next. This copy-specific relationship F takes into account the circumstance that the detectors of gas detection devices 100 of identical design may differ electrically and/or chemically. A correlation factor α, which is valid for one copy, is used as a relationship F in one embodiment. The linear relationship $Con=\alpha*\Delta U_{komp}$ is used in this embodiment. This relationship is stored in a memory 50 of the gas detection device 100.

This functional relationship F, which is preferably valid for a particular copy of a gas detection device 100, is adapted automatically in one embodiment to the quality parameter Q by applying a dimensionless correction factor β[Q]. The correction factor β[Q] preferably increases with decreasing quality parameter Q. As a result, a decreasing sensitivity of the gas detection device 100 is compensated by calculation to a certain degree. The adaptation to the quality parameter Q and hence the correction factor β[Q] are valid for a defined set of gas detection devices 100, for example, for a product line. The adaptation leads to the calculation rule $Con=\beta[Q]*F^{-1}(\Delta U_{komp})$.

For example, the correction factor β[Q] is used in addition to the correlation factor α. $Con=\beta[Q]*\alpha*\Delta U_{komp}$ in this embodiment.

Figure 13:
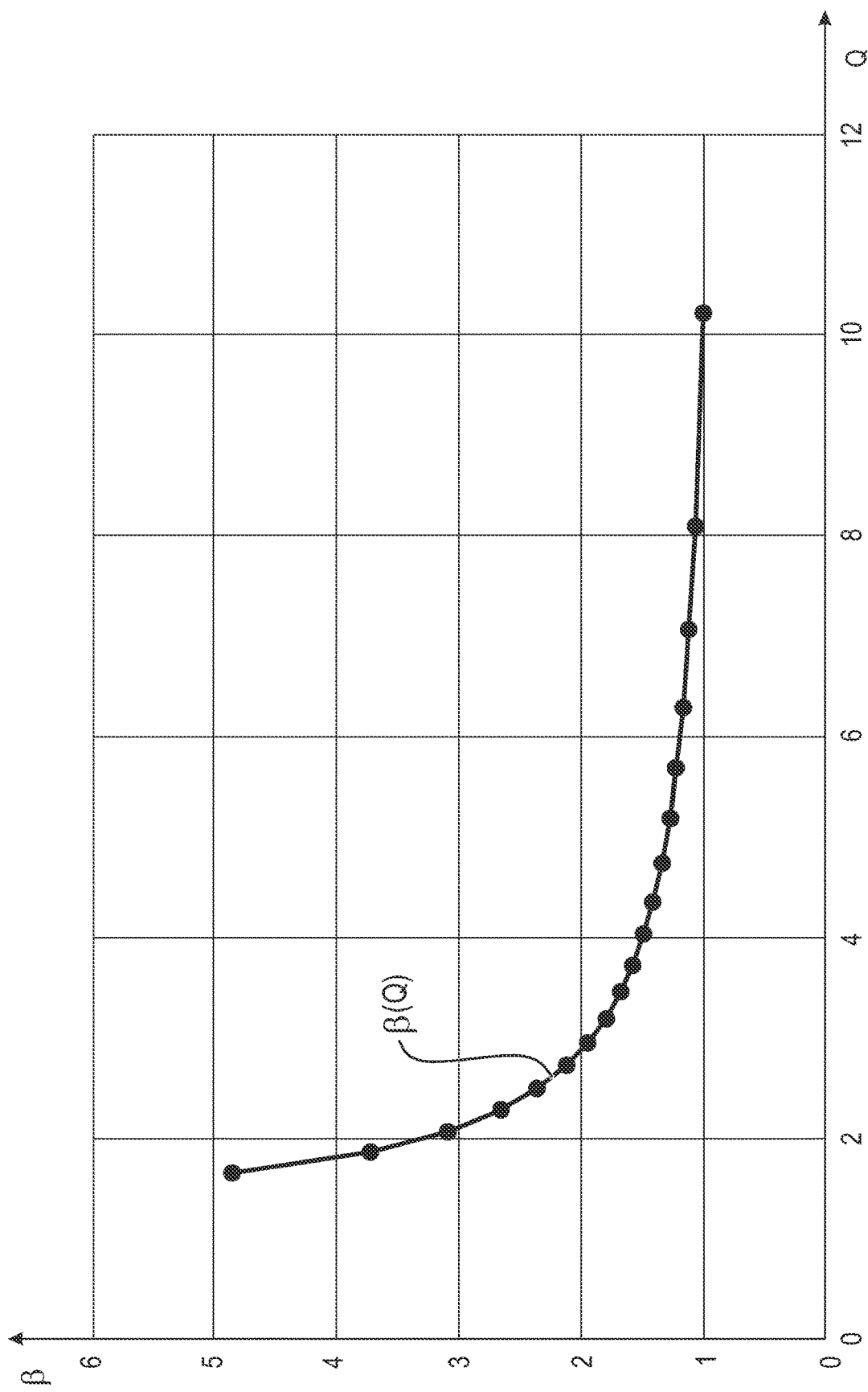
FIG. 13 is a graph showing an exemplary functional relationship between a factor for the target gas concentration and the quality parameter.

FIG. 13 shows as an example an empirically determined characteristic for the correction factor β=β[Q]. The quality parameter Q is plotted on the x axis and the resulting factor β=β[Q] on the y axis. A gas detection device 100 that is not poisoned at all has a quality parameter Q equaling 10 in this example, cf. FIG. 11. The quality parameter Q drops, for example, as is shown in FIG. 12, i.e., from right to left in FIG. 13. The correction factor β=β[Q] rises at least to the second power with dropping quality parameter Q. The gas detection device 100 is poisoned at a quality parameter Q below 1.8 to such a great extent that it cannot be used reliably any longer.

In one embodiment, the gas detection device 100 is put out of operation when the quality parameter Q drops below a predefined quality parameter threshold. In a preferred embodiment, the gas detection device 100 can, by contrast, be operated optionally in a normal mode or in an exceptional mode. The gas detection device 100 is preferably operated in the normal mode as long as the quality parameter Q is above the predefined quality parameter threshold in the presence of a combustible target gas, and in the exceptional mode otherwise. The gas detection device 100 is initially preferably in the normal mode and is switched automatically into the exceptional mode when the quality parameter Q becomes lower than the quality parameter threshold. Note: An increased number of false alarms may occur in the exceptional mode. The gas detection device 100 therefore preferably outputs a message when it is operating in the exceptional mode in order to be repaired or replaced. It is also possible that the gas detection device 100 outputs a message perceptible for a human being that the quality parameter Q is below the quality parameter threshold, and it switches over into the exceptional mode after a corresponding input or confirmation by a user.

If the quality parameter Q drops below the above-mentioned quality parameter threshold, the gas detection device 100 is switched automatically or also manually into the exceptional mode. An alternative embodiment of how the gas detection device 100 operates in the exceptional mode will be described below. This alternative embodiment also requires that the compensator 11 be capable of oxidizing target gas, i.e., it is also applicable to one of the embodiments according to FIG. 3 through FIG. 5. The electrical voltage U is the detection variable in this example as well.

On the one hand, two correlation factors, namely, a correlation factor $\alpha_{10}$ for the detector 10 and a correlation factor au for the compensator 11, are determined during an adjustment carried out in advance. These two correlation factors $\alpha_{10}$, $\alpha_{11}$ are preferably determined empirically for a single copy of a gas detection device 100.

Not only the detector 10 but also the compensator 11 are capable of oxidizing target gas in the embodiments according to FIG. 3 through FIG. 5. As was already described, the oxidation of a combustible target gas causes the temperature Temp_11 of the heating segment 30 of the compensator 11 to rise, and the electrical resistance R11 therefore rises as well and the detection variable U11 becomes higher based on the regulation of a constant current intensity I11. The correlation factor au, for the compensator 11 is therefore greater than zero.

In the embodiment according to FIG. 2, the compensator 11 is not capable of oxidizing target gas. A combustible target gas in the area around the compensator 11 therefore leads to cooling of the compensator 11 and to a reduction of the detection variable U11. Therefore, the correlation factor $\alpha_{11}$ for the compensator 11 is lower than zero.

In addition, two correction factors, namely, a factor $\beta_{10}$ for the detector 10 and a factor $\beta_{11}$ for the compensator 11, are determined in both embodiments. These two correction factors $\beta_{10}$, $\beta_{11}$ are valid for a set of gas detection devices 100 according to the present invention, for example, for a product line.

The concentration Con of the combustible target gas, which is being sought, is calculated in the exceptional mode according to the calculation rule $$Con=\beta_{10}[Q]*\alpha_{10}U10_{komp}+\beta_{11}[Q]*\alpha_{11}*U11_{komp}.$$

The correlation factors $\alpha_{10}$, $\alpha_{11}$ remain constant during the entire use time of the gas detection device 100. In a preferred embodiment, the two correction factors $\beta_{10}$, $\beta_{11}$ depend on the quality parameter Q, i.e., $$Con=\beta_{10}[Q]*\alpha_{10}*U10_{komp}+\beta_{11}[Q]*\alpha_{11}*U11_{komp}.$$

The lower the quality parameter Q, the higher is preferably each correction factor $\beta_{10}[Q]$, $\beta_{11}[Q]$.

This embodiment makes it possible for the gas detection device 100 to be capable of detecting a combustible target gas with a high reliability and of determining the concentration thereof even in case of a relatively intense poisoning of the detector 10. The gas detection device 100 is at least capable of detecting a target gas when the value, which is calculated according to the calculation rule $\beta_{10}[Q]*U10_{komp}+\beta_{11}[Q]*U11_{komp}$, is above a predefined threshold. Since the compensator 11 oxidizes less combustible target gas and/or is exposed to harmful gases to a lesser extent than the detector 10, the compensator 11 is also poisoned more slowly, and the presence of target gas in the housing 1 causes, depending on the configuration of the compensator 11, an increase or a decrease in the compensator temperature Temp_11.

As was mentioned already above, the concentration Con is calculated in the normal mode, by contrast, according to the calculation rule $Con=\alpha*\beta*\Delta U_{komp}$, preferably according to the calculation rule $Con=\alpha*\beta[Q]*\Delta U_{komp}$.

In one embodiment, the gas detection device 100 calculates the concentration of a combustible target gas at each scanning time according to both calculation rules, i.e., both according to $$Con=\alpha*\Delta U_{komp} \text{ or } Con=\beta[Q]*\alpha*\Delta U_{komp}$$

and according to $$Con=\alpha_{10}*U10_{komp}+\alpha_{11}*U11_{komp} \text{ or }$$

$$Con=\beta_{10}[Q]*\alpha_{10}*U10_{komp}+\beta_{11}[Q]*\alpha_{11}*U11_{komp}.$$

These two calculation rules lead, as a rule, to different results. As long as the two results differ in absolute value or as a percentage by less than a predefined threshold, the result of the calculation rule $Con=\alpha*\Delta U_{komp}$ or $Con=\beta[Q]*\alpha*\Delta U_{komp}$ is used. It is otherwise certain that the detector 10 is intensely poisoned, and the gas detection device 100 is switched into the exceptional mode and one of the calculation rules $$Con=\alpha_{10}*U10_{komp}+\alpha_{11}*U11_{komp} \text{ or } Con=\beta_{10}[Q]*U10_{komp}+\beta_{11}[Q]*U11_{komp}$$

is used.

Consequently, the switching is not carried out directly depending on the quality parameter Q, but depending on the difference between the two results for the concentration calculation.

FIG. 2 shows an embodiment of a gas detection device 100 in which the compensator 11 is not configured to oxidize a combustible target gas. The presence of a combustible target gas does not lead therefore to such a great increase in the compensator temperature Temp_11 compared to the increase in the detector temperature Temp_10. Some target gases have a higher thermal conductivity than air and therefore cause the compensator temperature Temp_11 to drop.

Even if the gas detection device 100 is configured as indicated in FIG. 2, an increasing poisoning of the detector 10 leads to a decreasing quality parameter Q in the presence of a combustible target gas, even though this decrease is not as great as it is shown in FIG. 11 and FIG. 12 for the gas detection device 100 according to FIG. 5, since the increasing poisoning reduces the detector temperature Temp_10. The gas detection device 100 then detects, when a combustible target gas with a good thermal conductivity is present, that the compensator temperature Temp_11 decreases and the voltage U11 applied to the compensator 11 therefore decreases as well. The compensated compensator voltage U11$_{komp}$ becomes negative in the embodiment according to FIG. 2. Based on the increasing poisoning of the detector 10, the detector temperature Temp 10 does not any longer increase as greatly as in case of an unpoisoned detector 10.

While specific embodiments of the invention have been shown and described in detail to illustrate the application of the principles of the invention, it will be understood that the invention may be embodied otherwise without departing from such principles.

| List of Reference Characters | |
|---|---|
| 1 | Stable housing of the gas detection device 100; it accommodates the detector 10 and the compensator 11; it has the opening Ö; it is enclosed by the outer housing 4 |
| 2 | Flame arrester in the opening Ö, configured, for example, as a metal grid and/or sintered plate |
| 3 | Electrical line or line array, which connects the detector 10 and the compensator 11 to the voltage source 42 and thereby supplies it with electrical energy |
| 4 | Outer housing of the gas detection device 100; it accommodates the inner housing 1, the optional electrical resistors R20 and R21, the sensors 40, 40.10, 40.11 as well as 41, 41.10, 41.11, the control device 6 with the analysis unit 9 and the voltage source 42; it has the opening Ö |
| 5 | Compensator chamber; it encloses the compensator 11 aside from the opening Ö2 or Ö3 in a fluid-tight manner |
| 6 | Signal-processing control device; it receives signals from the sensors 40.10, 40.11, 41.10 and 41.11; it actuates the switches 7.10, 7.11 and, if necessary, the electrical resistances R10 and R11; it comprises the analysis unit 9 |
| 7.10 | Switch, which pulses the current I10 in the electrical line 3 for the detector 10 |
| 7.11 | Switch, which pulses the current I11 in the electrical line 3 for the compensator 11 |
| 8 | Detector chamber; it occupies the area in the interior of the housing 1 which is located outside of the compensator chamber 5 |
| 9 | Signal-processing analysis unit; it receives measured values from the sensors 40, 40.10, 40.11; it determines the voltage difference ΔU; it detects a combustible target gas; it belongs to the control device 6 |
| 10 | Detector, arranged in the detector chamber 8; it comprises the heating segment 20, the ceramic jacketing 21, a coating 23 or embedding consisting of a catalytic material and the mounting plate 22; configured as a pellistor |
| 11 | Compensator; it comprises the heating segment 30 and the ceramic jacketing 31 and optionally likewise catalytic material 23; likewise configured as a pellistor in one embodiment |
| 12 | Optional additional detector, arranged in the compensator chamber 5 |
| 17 | Thermal insulation between the detector 10 and the compensator 11 |
| 20 | Helical, electrically conductive wire; it acts as the heating segment of the detector 10 |
| 21 | Ceramic jacketing around the wire 20; provided with a catalytic coating 23 |
| 22 | Mounting plate, which holds the wire 20 and the ceramic jacketing 21 |
| 23 | Coating of the ceramic jacketing 21 consisting of a catalytic material |
| 30 | Heating segment of the compensator 11 |
| 40.11 | Voltage sensor; it measures the electrical voltage U11, which is applied to the compensator 11 |
| 41 | Current intensity sensor; it measures the current intensity I3 in the line 3 |
| 41.10 | Current intensity sensor; it measures the current intensity I10 in the section of the line 3 that supplies the detector 10 with current |
| 41.11 | Current intensity sensor; it measures the current intensity I11 in the section of the line 3 that supplies the compensator 11 with current |
| 50 | Memory for the time course (time curve) of the quality parameter Q |
| 100 | Gas detection device according to the present invention; it comprises the housings 1 and 4, the detector 10, the compensator 11, the electrical line 3, the sensors 40.10, 40.11, 41.10, 41.11, the switches 7.10, 7.11, the control device 6 with the analysis unit 9 and the voltage source 42 |
| α | Empirically determined correlation factor between the concentration Con and the compensated voltage difference ΔU$_{komp}$; it is valid for one copy of a gas detection device 100 |
| α$_{10}$ | Empirically determined correlation factor between the concentration Con and the compensated detector voltage U10$_{komp}$; it is valid for one copy of a gas detection device 100 |
| α$_{11}$ | |
| β = β[Q] | Empirically determined correction factor between the compensated voltage difference ΔU$_{komp}$ and the target gas concentration Con; it increases with decreasing quality parameter Q; it is valid for a set of gas detection devices 100 according to the present invention |
| β$_{10}$ = β$_{10}$[Q] | Empirically determined correction factor between the compensated detector voltage U10$_{komp}$; it increases with decreasing quality parameter Q; it is valid for a set of gas detection devices 100 according to the present invention |

-continued

List of Reference Characters

| | |
|---|---|
| $\beta_{11} = \beta_{11}[Q]$ | Empirically determined correction factor between the compensated compensator voltage $U11_{komp}$; it increases with decreasing quality parameter Q; it is valid for a set of gas detection devices 100 according to the present invention |
| Con | Combustible target gas concentration to be determined |
| D = D(Q) | Tolerance value: The interval [−D, +D] or [0, +D] is the tolerance range: When the compensated voltage difference $\Delta U_{komp}$ is outside of this tolerance range, a target gas is detected. The lower the quality parameter Q, the lower is also the tolerance value D |
| F | Functional relationship between the target gas concentration Con and the compensated voltage difference $\Delta U_{komp}$ |
| I3 | Identical intensity I10 of the electrical current flowing through the detector 10 and the compensator 11 (Wheatstone bridge) |
| I3_ref | Reference value for the intensity I3 of the electrical current flowing through the detector 10 and the compensator 11; it is determined during the calibration; it is the command variable in the regulation in the Wheatstone bridge |
| I10 | Intensity of the electrical current flowing through the detector 10 |
| I11 | Intensity of the electrical current flowing through the compensator 11 |
| Ö | Opening in the housing 1, through which a gas mixture can flow from area B into the interior of the housing 1 and into which the flame arrester 2 is inserted |
| Ö2 | Opening in the compensator chamber 5; it overlaps the opening Ö in the housing 1 |
| Ö3 | Opening in the compensator chamber 5; it connects the compensator chamber 5 to the detector chamber 8 |
| Q | Quality parameter for the gas detection device 100; identical to $U10_{komp}/U11_{komp}$ in one embodiment |
| R10 | Electrical resistance of the detector 10; correlated with the temperature of the detector 10 |
| R11 | Electrical resistance of the compensator 11; correlated with the temperature of the compensator 11 |
| R20 | Component configured as an electrical resistor, which is connected parallel to the detector 10 |
| R21 | Component configured as an electrical resistor, which is connected parallel to the compensator 11 |
| Temp_10 | Temperature of the detector 10 |
| Temp_11 | Temperature of the compensator 11 |
| U0 | Zero voltage; it is the voltage difference $\Delta U$ when no target gas is present |
| D0, 10 | Detector zero voltage; electrical voltage applied to the detector 10 when no target gas is present |
| U0, 11 | Compensator zero voltage; electrical voltage applied to the detector 10 when no target gas is present |
| U0, 12 | Other detector zero voltage; electrical voltage applied to the additional detector 12 when no target gas is present [START] |
| U10 | Electrical voltage that is applied to the detector 10 |
| $U10_{komp}$ | Electrical voltage compensated by the detector zero voltage; applied to the detector 10; equal to U10 − U0, 10 |
| U11 | Electrical voltage applied to the compensator 11 |
| $U11_{komp}$ | Electrical voltage compensated by the compensator zero voltage, which is applied to the compensator 11; equal to U11 − U0, 11 |
| U12 | Electrical voltage applied to the additional detector 12 |
| $U12_{komp}$ | Electrical voltage compensated by the compensator zero voltage; applied to the additional detector 12; equal to U12 − U0, 12 |
| U42 | Electrical voltage of the voltage source 42 |
| $\Delta U$ | Measured difference between the voltage U10 applied to the detector 10 and the voltage U11 applied to the compensator 11 or the bridge voltage (U10 − U11)/2 |
| $\Delta U12$ | Measured difference between the voltage U12 applied to the additional detector 12 and the voltage U11 applied to the compensator 11 or the bridge voltage (U12 − U11)/2 |
| $\Delta U0$ | Zero voltage: Difference between the voltage U10 applied to the detector 10 and the voltage U11 applied to the compensator 11 or the bridge voltage (D10 − U11)/2 in the absence of target gas |
| $\Delta U0, 12$ | Zero voltage: Difference between the voltage U12 applied to the additional detector 12 and the voltage U11 applied to the compensator 11 or the bridge voltage (U12 − U11)/2 in the absence of target gas |
| $\Delta U_{komp}$ | Compensated voltage difference, equal to $\Delta U - \Delta U0$ |
| $\Delta U12_{komp}$ | Compensated voltage difference, equaling $\Delta U12 - \Delta U0, 12$ |

What is claimed is:

1. A gas detection device for monitoring an area for at least one combustible target gas to be detected, the gas detection device comprising:

a detector comprising a detector heating segment, which is heated when electrical current flows through the detector heating segment;

a compensator comprising a compensator heating segment, which is heated when electrical current flows through the compensator heating segment;

a sensor arrangement; and a signal-processing analysis unit;

wherein the gas detection device is configured to provide a fluidic connection between the detector and the area to be monitored and to provide a fluidic connection between the compensator and the area to be monitored;
wherein the gas detection device is configured:
to apply an electrical voltage to the detector so that an electrical current flows through the detector heating segment and heats the detector heating segment: and
to apply an electrical voltage to the compensator so that an electrical current flows through the compensator heating segment and heats the compensator heating segment;
wherein the detector is configured to oxidize the combustible target gas present in a gas detection device interior by heating the detector heating segment;
wherein the compensator is configured to oxidize the combustible target gas to a lesser extent than the detector or the compensator is configured to not be capable of oxidizing the combustible target gas or the gas detection device is configured such that a smaller quantity of the combustible target gas reaches the compensator than reaches the detector from the area to be monitored or the compensator is configured to oxidize the combustible target gas to a lesser extent than the detector and the gas detection device is configured such that a smaller quantity of the combustible target gas reaches the compensator than reaches the detector from the area to be monitored or the compensator is configured to not be capable of oxidizing the combustible target gas and the gas detection device is configured such that a smaller quantity of the combustible target gas reaches the compensator than reaches the detector from the area to be monitored;
wherein the sensor arrangement is configured to measure:
a detector detection variable, which depends on a temperature of the detector heating segment; and
a compensator detection variable, which depends on a temperature of the compensator heating segment;
wherein the analysis unit is configured
to determine whether or not the combustible target gas is present in the area to be monitored, based on the measured detector detection variable and the measured compensator detection variable; or
to determine a concentration of the combustible target gas in the area to be monitored, based on the measured detector detection variable and the measured compensator detection variable; or
to determine whether the combustible target gas is present in the area to be monitored or not and to determine a concentration of the combustible target gas in the area to be monitored, based on the detector detection variable and the compensator detection variable;
wherein the analysis unit is further configured to calculate at least once, based on a determined presence of the predefined combustible target gas, a quality parameter for a current quality of the gas detection device, based on the detector detection variable and the compensator detection variable, such that the quality parameter increases:
with a measured increase in the detector detection variable; and
with a measured decrease in the compensator detection variable.

2. A gas detection device in accordance with claim 1, wherein the analysis unit is configured to at least partially compensate for a decreasing sensitivity of the gas detection device for the combustible target gas depending on the calculated quality parameter.

3. A gas detection device in accordance with claim 1,
wherein the analysis unit is configured:
to determine a compensated detector detection variable as a deviation between the measured detector detection variable and a predefined detector reference value, wherein the measured detector detection variable assumes the detector reference value when no combustible target gas is present; and
to determine a compensated compensator detection variable, as a deviation between the measured compensator detection variable and a predefined compensator reference value, wherein the measured compensator detection variable assumes the compensator reference value when no combustible target gas is present;
wherein the analysis unit is configured:
to determine whether the combustible target gas is present in the area to be monitored or not, based on the compensated detector detection variable and the compensated compensator detection variable; or
to determine a concentration of the combustible target gas in the area to be monitored, based on the compensated detector detection variable and the compensated compensator detection variable; or
to determine whether the combustible target gas is present in the area to be monitored or not and to determine a concentration of the combustible target gas in the area to be monitored, based on the compensated detector detection variable and the compensated compensator detection variable;
wherein the analysis unit is configured to calculate the quality parameter such that the quality parameter increases:
with an increase in the compensated detector detection variable; and
with a decrease in the compensated compensator detection variable.

4. A gas detection device in accordance with claim 3, wherein the quality parameter is calculated as a quotient of the compensated detector detection variable and the compensated compensator detection variable.

5. A gas detection device in accordance with claim 3,
wherein the analysis unit is configured to determine the presence and/or the concentration of the target gas as a function of the compensated detector detection variable and the compensated compensator detection variable and, in addition, depending on a parameter,
wherein the parameter influences a sensitivity of the gas detection device for the combustible target gas and depends on the calculated quality parameter.

6. A gas detection device in accordance with claim 5, wherein the parameter is a factor that increases with a decrease in the quality parameter.

7. A gas detection device in accordance with claim 5,
wherein the analysis unit is configured to determine that the combustible target gas is present when a difference between the two compensated detection variables is outside of a predefined tolerance range,
wherein the predefined tolerance range depends on the calculated quality parameter.

8. A gas detection device in accordance with claim 7, wherein the predefined tolerance range becomes narrower as the calculated quality parameter decreases.

9. A gas detection device in accordance with claim 3,
wherein the analysis unit is configured to determine the concentration of the combustible target gas by applying a predefined functional relationship to values of the two compensated detection variables, wherein the analysis unit is further configured to change the predefined functional relationship depending on the quality parameter such that the determined concentration increases with a decrease in the quality parameter at equal values of the two compensated detection variables.

10. A gas detection device in accordance with claim 1, wherein also the compensator is configured to oxidize the combustible target gas present in the interior of the gas detection device by heating the compensator heating segment, so that the compensator is heated further, wherein the gas detection device is configured such that the detector oxidizes more of the combustible target gas than the compensator at equal concentration of the surrounding combustible target gas.

11. A gas detection device in accordance with claim 1, further comprising an additional detector; and a housing defining an opening, wherein the additional detector is located within the housing and the detector is located outside of the housing, wherein the additional detector comprises an additional detector heating segment, which is heated when electrical current flows through the additional detector heating segment, wherein the gas detection device is configured to apply an electrical voltage to the additional detector so that an electrical current flows through the additional detector heating segment and heats the additional detector heating segment, wherein the detector is configured to oxidize the combustible target gas present in the interior of the gas detection device by heating the additional detector heating segment, wherein the sensor arrangement is configured to measure an additional detector detection variable, which depends on the temperature of the additional detector heating segment, and wherein the analysis unit is configured to calculate the quality parameter such that the quality parameter increases:

with a measured increase in the detector detection variable or with a measured increase in the additional detector detection variable, or with a measured increase in the detector detection variable and with a measured increase in the additional detector detection variable; and with a measured decrease in the compensator detection variable.

12. A gas detection device in accordance with claim 11, wherein the analysis unit is configured to calculate a first individual quality parameter and a second individual quality parameter such that the first individual quality parameter increases as the detector detection variable increases and as the compensator detection variable decreases, and the second individual quality parameter increases as the additional detector detection variable increases and as the compensator detection variable decreases, and wherein the analysis unit is further configured to calculate the quality parameter depending on the first individual quality parameter and the second individual quality parameter.

13. A gas detection device in accordance with claim 12, wherein the analysis unit is configured to use the higher of the first individual quality parameter and the second individual quality parameter as the quality parameter.

14. A gas detection device in accordance with claim 1, further comprising a memory, wherein the analysis unit is configured to calculate the quality parameter for the current quality of the gas detection device anew as a response to a detection of the target gas and to store the quality parameter for the current quality of the gas detection device in the memory each time the combustible target gas is detected.

15. A gas detection device in accordance with claim 14, wherein the analysis unit is configured to determine a parameter for an accumulated previous loading of the detector with harmful gases, wherein the analysis unit is configured to store on the memory the quality parameter for the current quality of the gas detection device in connection with the parameter for the accumulated previous loading of the detector as a response to the detection of the combustible target gas.

16. A gas detection device in accordance with claim 1, wherein the analysis unit is configured to calculate the quality parameter as a response to a detection of the combustible target gas and to compare the calculated quality parameter with a predefined quality parameter threshold, wherein the gas detection device is configured to be operated in a normal mode or in an exceptional mode, and wherein the gas detection device is configured to switch over into the exceptional mode when the calculated quality parameter is below the quality parameter threshold, wherein the analysis unit in the normal mode is configured to measure the presence of the combustible target gas or the concentration of the combustible target gas, or both the presence of the combustible target gas and the concentration of the combustible target gas, as a function of a difference between the two detection variables, and wherein the analysis unit in the exceptional mode is configured to determine the presence of the combustible target gas or the concentration of the combustible target gas, or both the presence of the combustible target gas and the concentration of the combustible target gas depending on a weighted aggregation of the two detection variables.

17. A gas detection device in accordance with claim 16, wherein the weighting factor for the detector detection variable depends on the quality parameter.

18. A gas detection device in accordance with claim 17, wherein the weighting factor for the detector detection variable is higher as the quality parameter decreases.

19. A process for monitoring an area for at least one combustible target gas to be detected wherein the process comprises the step of:

providing a gas detection device comprising:

a detector comprising a detector heating segment, which is heated when electrical current flows through the detector heating segment; and a compensator comprising a compensator heating segment, which is heated when electrical current flows through the compensator heating segment;

establishing a fluidic connection between the detector and the area to be monitored and a fluidic connection between the compensator and the area to be monitored;

applying an electrical voltage to the detector so that an electrical current flows through the detector heating segment and the applied voltage heats the detector heating segment;

oxidizing the combustible target gas to be detected if present in an interior of the gas detection device by the heating of the detector heating segment;

applying an electrical voltage to the compensator so that an electrical current flows through the compensator heating segment and heats the compensator heating segment;

oxidizing the combustible target gas to be detected in an interior of the gas detection device, by the heating of the compensator heating segment, to a lesser extent than the oxidizing by the heating of the detector heating segment or not oxidizing the combustible target gas to be detected at all in the interior of the gas detection device, by the heating of the compensator heating segment, or configuring the gas detection device such that a smaller quantity of the combustible target gas reaches the compensator than reaches the detector from the area to be monitored;

measuring a detector detection variable, which depends on a temperature of the detector heating segment;

measuring a compensator detection variable, which depends on a temperature of the compensator heating segment;

carrying out at least one of:
 determining whether or not the predefined combustible target gas is present in the area to be monitored; and
 determining a concentration of the predefined combustible target gas in the area to be monitored; and calculating at least once a quality parameter for a current quality of the gas detection device, as a response to a determined presence of the combustible target gas, based on the detector detection variable and the compensator detection variable, wherein the quality parameter is calculated such that the quality parameter increases:
 as the measured detector detection variable increases; and
 as the measured compensator detection variable decreases.

* * * * *